US009044443B2

(12) United States Patent
Roberts et al.

(10) Patent No.: US 9,044,443 B2
(45) Date of Patent: *Jun. 2, 2015

(54) METHODS OF TREATING AUTISM

(71) Applicant: Clinical Research Associates LLC, New York, NY (US)

(72) Inventors: Kathryn Roberts, Cambridge, MA (US); Randall L. Carpenter, Cambridge, MA (US); Mark F. Bear, Cambridge, MA (US)

(73) Assignee: CLINICAL RESEARCH ASSOCIATES, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/912,874

(22) Filed: Jun. 7, 2013

(65) Prior Publication Data

US 2013/0261186 A1  Oct. 3, 2013

Related U.S. Application Data

(63) Continuation of application No. 13/614,715, filed on Sep. 13, 2012, now abandoned, which is a continuation of application No. 13/362,985, filed on Jan. 31, 2012, now Pat. No. 8,278,276, which is a continuation of application No. 12/454,202, filed on May 14, 2009, now Pat. No. 8,143,311, which is a continuation of application No. PCT/US2007/024311, filed on Nov. 21, 2007.

(60) Provisional application No. 60/860,733, filed on Nov. 22, 2006, provisional application No. 61/001,567, filed on Nov. 2, 2007.

(51) Int. Cl.
*A61K 38/00* (2006.01)
*A61K 31/197* (2006.01)
*A61K 31/195* (2006.01)
*A61K 31/215* (2006.01)
*A61K 31/428* (2006.01)

(52) U.S. Cl.
CPC .............. *A61K 31/197* (2013.01); *A61K 31/195* (2013.01); *A61K 31/215* (2013.01); *A61K 31/428* (2013.01)

(58) Field of Classification Search
None
See application file for complete search history.

(56) References Cited

U.S. PATENT DOCUMENTS

| | | | |
|---|---|---|---|
| 6,455,553 B1 | 9/2002 | Werner et al. | |
| 6,656,172 B1 | 12/2003 | Hildebrand | |
| 6,890,931 B2 | 5/2005 | Bear et al. | |
| 6,916,821 B2 | 7/2005 | Bear et al. | |
| 7,648,993 B2 | 1/2010 | Bear et al. | |
| 2003/0216293 A1 | 11/2003 | Eriksson | |
| 2005/0107334 A1 | 5/2005 | Gallop et al. | |
| 2005/0171067 A1 | 8/2005 | Bear et al. | |
| 2006/0058241 A1 | 3/2006 | Geier et al. | |
| 2006/0058271 A1 | 3/2006 | Geier et al. | |
| 2006/0247728 A1 | 11/2006 | Foster et al. | |
| 2007/0191440 A1 | 8/2007 | Solomon et al. | |
| 2007/0254314 A1 | 11/2007 | Geier et al. | |
| 2012/0129773 A1 | 5/2012 | Geier et al. | |

FOREIGN PATENT DOCUMENTS

| | | |
|---|---|---|
| EP | 1094830 A1 | 5/2001 |
| EP | 1392363 A2 | 3/2004 |
| WO | WO-02078745 A2 | 10/2002 |
| WO | WO-2005002559 A2 | 1/2005 |
| WO | WO-2005025559 A1 | 3/2005 |
| WO | WO-2006012403 A1 | 2/2006 |
| WO | WO-2006121919 A2 | 11/2006 |
| WO | WO-2007029063 A2 | 3/2007 |
| WO | WO-2007053596 A1 | 5/2007 |
| WO | WO-2011056849 A1 | 5/2011 |

OTHER PUBLICATIONS

Best 2007 (J Neurophysiol 97:892-900).
Fisher 2003 (Journal of Molecular Neuroscience 20:349-356).
El Idrissi 2005 (Neuroscience Letters 377:141-146).
Riedel 2009 Behavioural Brain Research 204:217-225.
International Search Report for PCT/US2007/024311, Date of Issuance May 26, 2009.
International Preliminary Report on Patentability for PCT/US2007/024311, Date of Issuance May 26, 2009.
Bear, M.F., et al., "The mGluR Theory of Fragile X Mental Retardation," Opinion: Trends in Neurosciences, 27(7):370-377 (2004).
Australian Patent Application No. 2007325836, Examiner's First Report, from the Australian Government IP Australia, Feb. 16, 2010.
Australian Patent Application No. 2007325836. Official Notice of Acceptance from the Australian Government IP Australia, Jul. 6, 2011.
Ciccaglione, A.F., Effect of Acute and Chronic Administration of the GABA(B) Agonist Baclofen on 24 Hour pH Metry and Symptoms in Control Subjects and in Patients with Gastro-Oesophageal Reflux Disease, Gut, 52:464-470 (2003).
European Patent Application No. 07862184.4, Office Action from the European Patent Office, Jan. 3, 2011.
Kawai, M., et al., "Effect of Baclofen on Emesis and 24-Hour Esophageal pH in Neorologically Impaired Children with Gastroesophageal Reflux Disease," Journal aof Pediatraic Gastroenterology and Nutrition, 38:317-323 (Mar. 2004).
Kelleher, R.J., III and Bear, M.F., "The Autistic Neuron: Troubled Translation?" Cell, 135:401-406 (2008).
Koek, G.H., et al., "Effect of the GABA(B) Agonist Baclofen in Patients with Symptoms and Duodeno-Gastro-Oesophageal Reflux Refractory to Proton Pump Inhibitors," Gut, 52:1397-1402 (2003).
Krueger, D.D and Bear, M.F., "Toward Fulfilling the Promise of Molecular Medicine in Fragile X Syndrome," Annu. Rev. Med., 62:31.1-31.19 (2011).

(Continued)

Primary Examiner — Daniel E Kolker
Assistant Examiner — Stacey N MacFarlane
(74) Attorney, Agent, or Firm — Fox Rothschild LLP

(57) ABSTRACT

Subjects having autism are treated with a composition that includes gamma-aminobutyric acid agonists. The gamma-aminobutyric acid agonist (GABA) can be a GABA(B) agonist, such as baclofen. The humans can be administered the GABA(B) agonist in a single dose or multiple doses.

6 Claims, 7 Drawing Sheets

(56) References Cited

OTHER PUBLICATIONS

Lidums, I., et al., "Control of Transient Lower Esophageal Sphincter Relaxations and Reflux by the GABA(B) Agonist Baclofen in Normal Subjects," Gastroenterology 118(1):7-13 (Jan. 2000).
Pacey, L.K.K., et al., "Subchronic Administration and Combination Metabotropic Glutamate and GABAB Receptor Drug Therapy in fragile X Syndrome," JPET Fast Forward, pp. 1-34. Published on Jun. 2, 2011.
Primrose, D.A., "Treatment of Self-Injurious Behaviour with A GABA (Gamma-Aminobutyric Acid) Analogue," J. Ment. Defic. Res., 23:163-173 (1979).
Van Herwaarden, M.A., et al., "The Effect of Baclofen on Gastro-Oesophageal Sphincter Function and Reflux Symptoms in Patients with Refulx Disease," Aliment Pharmacol. Ther., 16(9):1655-62 (Sep. 2002).
Volk, L.J., et al., "Multiple Gq-Coupled Receptors Converge on a Common Protein Synthesis-Dependent Long-Term Depression That is Affected in Fragile X Syndrome Mental Retardation," Journal of Neuroscience, 27(43):11624-11634 (Oct. 2007).
Wise, J. and J.L. Conklin, "Review Gastroesophageal Reflux Disease and Baclofen: Is There Light at the End of the Tunnel?" Cuff. Gastroenterol. Rep. 6(3):213-219 (Jun. 2004).
Zhang, Q., et al., "Control of Transient Lower Oesophageal Sphincter Relaxations and Reflux by the GABA(B) Agonist Baclofen in Patients with Gastro-Oesphageal Reflux Disease," Gut, 50(1):19-24 (Jan. 2002).
Zupan, B., et al., "Neurobiological Basis of Hyperactivity in the FMRP KO Mouse," Program No. 579.8, 2005 Abstract Viewer/Itinerary Planner, Washington, DC; Society for Neuroscience, 2005. Online.
Kadyan 2003 (American Journal of Physical Medicine & Rehabilitation 82:560-562).
Cohen 2002 (Medical Hypotheses 59(1):115-116.
Roth, C.L. et al., "Antagonistic and Agonistic GnRH Analogue Treatment of Precocious Puberty: Tracking Gonadotropin Concentrations in Urine," Horm Res, 63:257-262 (2005).
Amikishieva, A. V., "Testosterone and Behavior: Involvement of the Hormone in Psychotropic Effects of Baclofen," Bulletin of Experimental Biology and Medicine, 143(2): 259-263 (2007).
Cherek, D. R., et al. "Acute Effects of Baclofen, a .gamma.-Aminobutyric Acid-B Agonist, on Laboratory Measures of Aggressive and Escape Responses of Adult Male Parolees With and Without a History of Conduct Disorder," Psychopharmacology,164:160-167 (2002).
Paredes, R. and Agmo, A., "Stereospecific Actions of Baclofen on Sociosexual Behavior, Locomotor Activity and Motor Execution," Psychopharmacology 97(3): 358-364 (1989).
Mandema, J. W., et al., "Modeling of the Effect Site Equilibration Kinetics and Pharmacodynamics of Racemic Baclofen and its Enantiomers Using Quantitative EEG Effect Measures," J Pharmacol Exp Ther, 261(1):88-95 (1992).
Eaton, G. G., et al., "Self-Injurious Behavior is Decreased by Cyproterone Acetate in Adult Male Rhesus (Macaca Mulatta)," Hormones and Behavior, 35:195-203 (1999).
Baron-Cohen, S., et al., "Sex Differences in the Brain: Implications for Explaining Autism," Science, 310(5749):819-823 (2005).
Jackson, G. L., et al., "A .gamma.-Aminobutyric Acid.sub.B Agonist Reverses the Negative Feedback Effect of Testosterone on Gonadotropin-Releasing Hormone and Luteinizing Hormone Secretion in the Male Sheep," Endocrinology, 141(11):3940-3945 (2000).
Tordjman, S., et al., "Androgenic Activity in Autism," Am J Psychiatry, 154(11):1626-1627 (1997).
Kadyan, V., et al., "Intrathecal Baclofen for Spasticity Management in Rett Syndrome," Am. J. Phys. Med. Rehabil., 82(7): 560-562 (Jul. 2003).
Fromm, G.H., et al., "Comparision of L-Baclofen and Racemic Baclofen in Trigeminal Neuralgia," Neurology, 37:1725-1728 (1987).

METHODS OF TREATING AUTISM

RELATED APPLICATIONS

This application is a continuation of U.S. application Ser. No. 13/614,715, filed Sep. 13, 2012, which is a continuation of U.S. application Ser. No. 13/362,985, filed Jan. 31, 2012 (now U.S. Pat. No. 8,278,276), which is a continuation of U.S. application Ser. No. 12/454,202, filed May 14, 2009 (now U.S. Pat. No. 8,143,311), which is a continuation of International Application No. PCT/US2007/024311, filed Nov. 21, 2007, which designates the U.S., published in English, and claims the benefit of U.S. Provisional Application No. 61/001,567, filed Nov. 2, 2007, and U.S. Provisional Application No. 60/860,733, filed Nov. 22, 2006. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

a) File name: 39331008015SequenceListing.txt; created Jun. 6, 2013, 2 KB in size.

BACKGROUND OF THE INVENTION

Mental retardation, Down's syndrome, fragile X syndrome and autism are developmental and genetic disorders that affect day to day functioning, including learning, memory, speech, social skills and behavior. Currently available treatment regimens for humans with mental retardation, Down's syndrome, fragile X syndrome and to assist in day-to-day functioning, include, for example, behavioral modifications and treatment with a range of medications including anti-depressant and anti-psychotic drugs. However, such regimens frequently are not effective or may produce undesirable side-effects with long term use, particularly the use of anti-psychotic drugs. Thus, there is a need to develop new, improved and effective methods to treat mental retardation, Down's syndrome, fragile X syndrome and autism.

SUMMARY OF THE INVENTION

The present invention relates to a method of treating humans having mental retardation, Down's syndrome, fragile X syndrome and autism.

In one embodiment, the invention is a method of treating a human, comprising the step of administering to a human having at least one condition selected from the group consisting of Down's syndrome, fragile X syndrome and autism a composition that includes a gamma-aminobutyric acid agonist.

In another embodiment, the invention is a method of treating a human, comprising the step of administering to a human having at least one condition selected from the group consisting of Down's Syndrome, fragile X syndrome and autism a composition that includes Formula I:

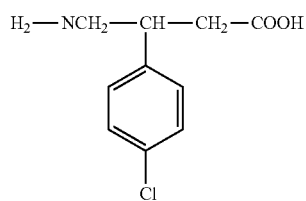

In yet another embodiment, the invention is a method of treating a human, comprising the step of administering to a human having at least one condition selected from the group consisting of mental retardation, Down's syndrome, fragile X syndrome and autism a composition that includes baclofen, wherein the baclofen is administered to the human at a dose of about 2 mg per day for days 1, 2 and 3 of treatment, a dose of about 4 mg per day for days 4, 5 and 6 of treatment, a dose of about 6 mg per day for days 7, 8 and 9 of treatment, a dose of about 10 mg per day for days 10, 11 and 12 of treatment, a dose of about 20 mg per day for days 13, 14 and 15 of treatment, a dose of about 30 mg per day for days 16, 17 and 18 of treatment and a dose between about 30 mg to about 80 mg per day for the duration of the treatment.

In an additional embodiment, the invention is a method of treating a human, comprising the step of administering to a human having at least one condition selected from the group consisting of mental retardation, Down's syndrome, fragile X syndrome and autism a composition that includes baclofen, wherein the baclofen is administered to the human at a dose of about 15 mg for days 1, 2 and 3 of treatment, a dose of about 30 mg for days 4, 5 and 6 of treatment, a dose of about 45 mg for days 7, 8 and 9 of treatment, a dose of about 60 mg for days 10, 11 and 12 of treatment and a dose between about 60 mg to about 80 mg per day for the duration of the treatment.

In still another embodiment, the invention is a method of treating a human, comprising the step of administering to a human having at least one condition selected from the group consisting of mental retardation, Down's syndrome, fragile X syndrome and autism a composition that includes at least about 51 mole percent S-baclofen relative to the total S-baclofen and R-baclofen in the composition administered to the human.

In a further embodiment, the invention is a method of treating a human, comprising the step of administering to a human having at least one condition selected from the group consisting of mental retardation, Down's syndrome, fragile X syndrome and autism a composition that includes at least about 51 mole percent R-baclofen relative to the total R-baclofen and S-baclofen in the composition administered to the human.

An additional embodiment of the invention is a method of treating a human, comprising the step of administering to a human having at least one condition selected from the group consisting of mental retardation, Down's syndrome, fragile X syndrome and autism a composition that includes baclofen, wherein the baclofen is administered to the human at a dosing regimen of at least one member selected from the group consisting of about 1 mg twice a day, about 2 mg twice a day, about 3 mg twice a day, about 5 mg twice a day, about 10 mg twice a day and about 10 mg three times a day.

In yet another embodiment, the invention is a method of treating a subject, comprising the step of administering to a subject having at least one condition selected from the group consisting of mental retardation, Down's syndrome, fragile X syndrome and autism a composition that includes at least one M1 muscarinic antagonist.

Advantages of the claimed invention can include, for example, treatment of mental retardation, Down's syndrome, fragile X syndrome and autism in a manner that can improve symptoms (e.g., reduce anxiety and irritability; increase cognitive function, communication and/or social interaction), efficacy or reduce side effects and thereby improve tolerability for use over a relatively long period of time without significant side effects. The methods of the invention can provide an effective manner to treat a subject having mental retardation, Down's syndrome, fragile X syndrome and/or autism.

DETAILED DESCRIPTION OF THE INVENTION

Figure 1:
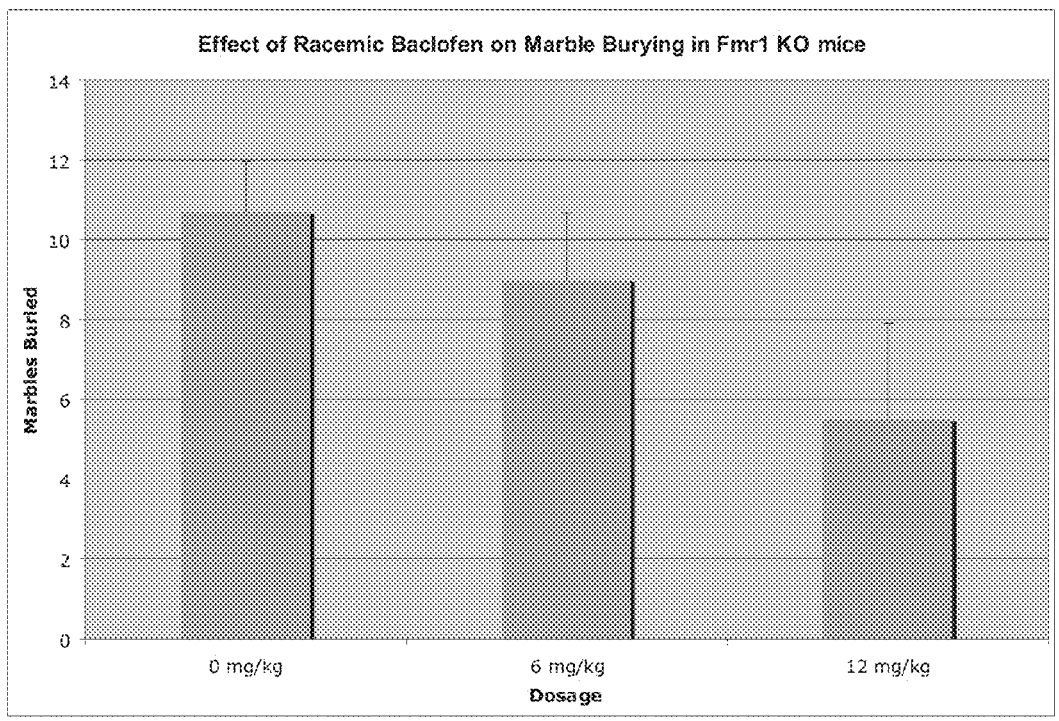
FIG. 1 depicts the effects of racemic baclofen on the inhibition of marble-burying behavior in fragile X (Fmr1) knock out (KO) mice (n=7-8 mice/group). Data are expressed as the mean±SEM number of marbles buried.

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

In one embodiment, the invention is a method of treating a human, comprising the step of administering to a human having at least one condition selected from the group consisting of Down's syndrome, fragile X syndrome and autism a composition that includes a gamma-aminobutyric acid (GABA) agonist, such as a GABA(B) receptor agonist (also referred to herein as "GABA(B) agonist" or "GABAB agonist").

GABA (gamma-amino butyric acid) is an abundant neurotransmitter in the mammalian brain. GABA, like other neurotransmitters, including L-glutamate, serotonin and acetylcholine, activates ionotropic and metabotropic receptors. Ionotropic receptors are ligand gated ion channels that convey fast synaptic transmission, whereas G-protein coupled metabotropic receptors modulate synaptic transmission through intracellular effector systems. GABA exerts its effects through ionotropic ligand-gated GABA(A) (also referred to as "GABAA"), GABA(C) (also referred to as "GABAC") and GABA(B) (also referred to as "GABAB") receptors to produce slow, and prolonged synaptic inhibitory signals by activating a Cl-conductance that can be allosterically modulated by psychoactive drugs, such as the benzodiazepines, barbiturates and neurosteroids.

The subunits of the GABA(A) receptor have sequence homology with the nAChR subunit family. A family of GABA(A) receptors subtypes exists, which are generated by alternative splicing of alpha 1-6, beta 1-4, gamma 1-4, delta, epsilon, pie, theta, and rho1-3 to form protein complexes. Various GABA(A) subunits show distinct patterns of temporal and spatial expression that may have tissue specific physiological roles. GABA(A) receptor proteins are characterized by the presence of a cleavable signal peptide, a large extracellular N-terminus, three transmembrane domains, a large cytoplasmic domain followed by another transmembrane domain and C-terminal extracellular domain. The other common motif is referred to as a Cys-loop and two Cys loops are separated by thirteen amino acids in the extracellular domain of the receptor. The regions between the third and fourth transmembrane domain and the large cytoplasmic loop are least conserved among various GAA subunits, which may confer subunit specific functionality. GAA genes are distributed as clusters throughout the human genome (chromosomes 4, 5, 15, and X; delta subunit on chromosome 1).

GABA(B) receptors are metabotropic transmembrane receptors for gamma-aminobutyric acid (GABA) that are linked by G-proteins to potassium channels (Chen K, et al., *Brain Res Bull* 67: 310-8 (2005)). GABA(B) receptors are found in the central and peripheral autonomic nervous system. GABA(B) receptors can stimulate potassium channels, which can result in hyperpolarization of the neuron, prevent sodium channel influx and, thus, neurotransmitter release. GABA(B) receptors may also reduce adenylyl cyclase activity and decrease calcium conductance in a neuron.

GABA(B) receptors are structurally similar to metabotropic glutamate receptors and are divided into two subtypes GABA(B)1 and GABA(B)2, which appear to assemble as heterodimers in neuronal membranes by linking by carboxytermini.

An "agonist," as used herein, is a compound that activates cell signaling. For example, a GABA(B) receptor agonist activates cell signaling mediated through GABA(B) receptors and an α2-adrenergic agonist activates cell signaling mediated through α2-adrenergic receptors.

The GABA agonists employed in the methods of the invention preferably cross the blood brain barrier. The GABA agonists for use in the methods described herein can inhibit glutamate release in the central nervous system, such as in the cortex and basal ganglia of the central nervous system.

In another embodiment, the invention is a method of treating a human, comprising the step of administering to a human having at least one condition selected from the group consisting of mental retardation, Down's Syndrome, fragile X syndrome and autism a composition that includes Formula I:

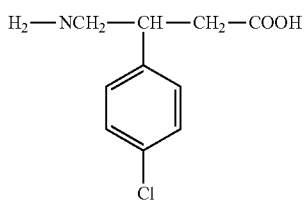

Formula I is baclofen, which is also referred to as β-(Aminomethyl)-4-chlorobenzenepropanoic acid; β-(aminomethyl)-p-chlorohydrocinnamic acid; γ-amino-β-(p-chlorophenyl)butyric acid; β-(4-chlorophenyl)GABA. Baclofen is also referred to as Baclon, Lioresal, Kemstro and Myospan.

The methods of the invention can include the use of a GABA(B) receptor agonist in combination with, for example, Formula II:

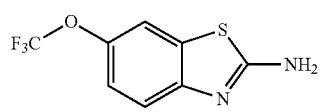

Formula II is 2-amino-6-trifluormethoxybenzothiazole and is also referred to herein as "riluzole" (see, for example, U.S. Pat. No. 4,370,338, the teachings of which are hereby incorporated by reference in its entirety).

Formula II is FDA approved for the treatment of amyotrophic lateral sclerosis. It has multiple activities, including inhibition of presynaptic glutamate release by inactivation of P/Q-type calcium channels, enhancement of glutamate uptake in astrocytes, and inhibition of voltage-dependent sodium channels in mammalian CNS neurons. It has also been reported to potentiate AMPA/KA receptor-mediated transmission, as well as enhance brain-derived neurotrophic factor. Riluzole has been shown to have neuroprotective, anticonvulsant activity, anti-anxiety activity, and antidepressant activity in animal models and in humans.

The subject can be treated with salts (e.g., acid salts, base salts, HCl, oxaylate, calcium, sodium, magnesium, lithium), prodrugs, polymorphs and other structural and functional derivatives thereof of the compounds, such as Formulas I and II, described herein.

Mental retardation means that a subject has lower than average intelligence. Intelligence describes a subject's ability to think, learn and solve problems. A subject with mental retardation may have difficulty learning, may take longer to learn social skills, such as how to communicate, and may be less able to care for himself or herself and to live on his or her own as an adult.

Down's syndrome is a disorder that includes a combination of birth defects, including some degree of mental retardation, characteristic facial features and, often, heart defects, increased infections, problems with vision and hearing, and other health problems. The severity of these problems varies greatly among affected subjects. Down's syndrome is generally is caused by an extra copy chromosome 21 and is also referred to as trisomy 21.

The fragile X syndrome, as implied by its name, is associated with a fragile site expressed as an isochromatid gap in the metaphase chromosome at map position Xq 27.3. Fragile X syndrome is a genetic disorder caused by a mutation in the 5'-untranslated region of the fragile X mental retardation 1 (FMR1) gene, located on the X chromosome. The mutation that causes fragile X syndrome is a associated with a CGG repeat in the fragile X mental retardation gene FMR-1. When a subject has more than about 200 CGG repeats, the fragile X gene is hypermethylated, silenced, fragile X mental retardation protein (FMRP) is not produced and the subject is diagnosed as having fragile X syndrome (See, for example, U.S. Pat. Nos. 6,107,025 and 6,180,337, the entire teachings of both of which are hereby incorporated by reference in their entirety).

The fragile X syndrome segregates as an X-linked dominant disorder with reduced penetrance. Either sex when carrying the fragile X mutation may exhibit mental deficiency, which is variable in severity.

Children and adults with fragile X syndrome have varying degrees of mental retardation or learning disabilities and behavioral and emotional problems, including autistic-like features and tendencies. Young children with fragile X syndrome often have delays in developmental milestones, such as learning how to sit, walk and talk. Affected children may have frequent tantrums, difficulties in paying attention, frequent seizures (e.g., temporal lobe seizures) are often highly anxious, easily overwhelmed, can have sensory hyperarousal disorder, gastrointestinal disorders, may have speech problems and unusual behaviors, such as hand flapping and hand biting.

Fragile X syndrome can be diagnosed by an established genetic test performed on a sample (e.g., blood sample, buccal sample) from the subject. The test determines whether a mutation or pre-mutation is present in the FMR-1 gene of the subject.

Subjects with fragile X syndrome can also have autism, attention deficit disorder and/or obsessive compulsive disorder. Fragile X syndrome is a prevalent form of inherited mental retardation and is characterized by developmental delay, hyperactivity, attention deficit disorder and autistic-like behaviors (Jin, P., et al., Hum Mol Genet. 9: 901-908 (2000)).

About 5% of all children diagnosed with autism have a mutation in the FMR1 gene and also have fragile X syndrome (FXS). About 15 to about 20% of subjects with fragile X syndrome meet the full diagnostic criteria for autism. Although mental retardation is a hallmark feature of fragile X syndrome, subjects with fragile X syndrome often display autistic features ranging from shyness, poor eye contact, and social anxiety in mild cases to hand flapping, hand biting and perseverative speech in the severely affected. Subjects with fragile X syndrome display other symptoms associated with autism such as attention deficit and hyperactivity, seizures, hypersensitivity to sensory stimuli obsessive-compulsive behavior and altered gastrointestinal function. The FMR1 mutation prevents expression of a single protein (FMRP). Brain development in the absence of FMRP gives rise to the major symptoms of fragile X syndrome. A key tool allowing for a better understanding of the function of FMRP has been development of the Fmr1 knockout mouse.

In addition to core symptoms, children with fragile X syndrome frequently have serious behavioral disturbances such as irritability, aggression and self-injurious behaviors. In a recent study of males with fragile X syndrome (ages 8-24), self-injurious behavior was reported in 79%, and aggressive behavior in 75%, of subjects during a two month observation period (Hessl, D., et al., *The National Fragile X Foundation Quarterly*, Issue 25:10-13 (2006)). Despite the common occurrence of irritable, aggressive and self-injurious behavior in subjects with fragile X syndrome, there has been little research assessing treatments for these symptoms.

Although there has been little research in subjects with fragile X syndrome, serious behavioral disturbances such as self-injurious behavior, aggression and tantrums occur frequently in individuals with autism (McCracken, J. T., et al., *N. Engl. J. Med.* 347:314-321 (2002)), and there have been numerous clinical trials assessing a variety of therapeutic treatments. Behavior therapy may provide benefits, but is highly individualized and has not been evaluated in randomized clinical trials (Schreibman, L., *J. Autism Dev. Discord.* 5:373-378 (2002)). Similarly, treatments with several medications in various chemical classes have had limited success (McDougle, C. J., et al., *Child Adolesc. Psychiatr. Clin. N. Am.* 9:201-224 (2002)). Risperidone, an atypical antipsychotic, has been used to treat behaviors in subjects with autism (McCracken, J. T., et al., *N. Engl. J. Med.* 347:314-321 (2002)). However, risperidone produces a number of undesirable side effects including increased appetite (73%) and weight gain (2.7 kg over 8 weeks), fatigue (59%), drowsiness (49%), drooling (27%), and dizziness (16%) (McCracken, J. T., et al., *N. Engl. J. Med.* 347:314-321 (2002)). There are also unresolved safety concerns that long-term therapy may cause extrapyramidal symptoms and that elevated prolactin levels may affect growth and sexual maturation. These side effects limit tolerability and usefulness of risperidone alone for treating irritable aberrant behavior in subjects with autism.

Formal studies have not been published in subjects with fragile X syndrome, however clinical experience with atypical antipsychotics, such as risperidone alone is consistent with the results observed in subjects with autism (McCracken, J. T., et al., *N. Engl. J. Med.* 347:314-321 (2002); Berry-Kravis, E., et al., *Ment. Retard. Devel Disabil. Res. Rev.* 10:42-48 (2004)). Specifically, risperidone alone reduces irritable behavior, but the side effect profile limits use of it alone in subjects with fragile X syndrome.

Initial studies of the behavioral phenotype of the Fmr1 KO mouse on a mixed genetic background reported that the Fmr1 KO mice displayed increased exploratory and locomotor activity compared to wild-type controls, and also a slight learning impairment in the Morris water maze (Bakker, C. E., et al., *Cell* 78:23-33 (1994)). This learning impairment has been further analyzed by several groups using the Morris water task, plus-shaped water maze, operant conditioning paradigms, conditioned fear, passive avoidance and the radial maze (Bakker, C. E., et al., *Cell* 78:23-22 (1994). Fmr1 KO mice have impaired learning processes when assessed on assays that had previously not been attempted. Fmr1 KO mice do have impaired learning that is clearly task dependent. It is likely that learning and memory performance of Fmr1 KO mice is dependent on genetic background (Paradee, W., et al., *Neuroscience* 94:185-192 (1999)). Although the learning and memory phenotype of the Fmr1 KO mouse has been challenging and somewhat elusive, there are sufficient data indicating that Fmr1 KO mice are hyperactive, have altered responses on tests of anxiety, and altered sensorimotor gating (Mineur, Y. S., et al., *Hippocampers* 12:39-46 (2002)). FMRP can regulate behavioral states of activity/arousal, anxiety-related responses, and social interactions (Bakker, C. E., et al., *Cell* 78:23-33 (1994); Peier, A. M., et al., *Hum. Mol. Genet.* 9:1145-1159 (2000)).

By challenging the Fmr1 KO mice with different test situations, the KO mice are hyperactive, can display increased anxiety-like responses, do show abnormal social interactions, and have poor learning and memory. Fmr1 KO mice display several abnormal behavioral responses that parallel symptoms of FXS. Behavioral responses of Fmr1 KO mice depend on genetic background. Fmr1 KO mice on particular genetic backgrounds display increased 'autistic-like' traits. Specifically, Fmr1 KO mice on a C57BL/6J X DBA/2 F1 (D2-Fmr1 F1) hybrid background display increased stereotypies in the open-field, increased obsessive-like responding in the marble-burying task, and have reduced social interactions, while Fmr1 KO mice on a C57BL/6J X 129S1/SvImJ F1 (129-Fmr1 F1) hybrid background appear to have poor social recognition. That only some of the Fmr1 KO strains display increased 'autistic-like' traits is consistent with the observations that only 15-20% of FXS individuals have autism, and may have variation in FXS due to genetic background. Other mouse models of FXS can display unique autistic-like features. (Spencer, C. M., et al., *Genes, Brain and Behavior*, 4:420-430 (2005)).

Cognitive behavioral therapy has been used to improve language and socialization in fragile X syndrome and autism. In addition, many classes of psychiatric drugs are used in clinical practice to treat symptoms and behavior in both populations (Berry-Kravis, E. et al., *Ment. Retard. Devel Disabil. Res. Rev.* 10:42-48 (2004); Malone, R. P., et al., *CNS Drugs* 19:923-924 (2005)). In recent years, pharmacological treatment with the atypical antipsychotic risperidone has been commonly employed to augment non-pharmacological approaches in the treatment of individuals with autism. A randomized placebo-controlled trial of risperidone in autistic children demonstrated significant improvement on the irritability subscale of the Aberrant Behavior Checklist and the Clinical Global Impressions-Improvement (McCracken, J. T., et al., *N. Engl. J. Med.* 347:314-321 (2002)). However, adverse events included weight gain, increased appetite, fatigue, drowsiness, dizziness, and drooling. Social isolation and communication were not improved by administration of risperidone and adverse side effects such as extrapyramidal symptoms and dyskinesias have been associated with risperidone use in autistic children (Malone, R. P., et al., *J. Am. Acad. Child Adolsecent. Psychiatry* 41:140-147 (2002)).

Although a number of other drugs, including antipsychotics, antidepressants, and anticonvulsants have mixed results in treating various symptoms and behaviors associated with autism and fragile x syndrome; there is a need to develop new treatments.

As described herein, R-baclofen may be more potent than S-baclofen for reducing obsessive-compulsive and repetitive behavior, and for reducing audiogenic seizures, with minimal side effects. R-baclofen may be useful for the management of typical problem behavior, such as irritability and aggression, in humans with fragile X syndrome. Baclofen may improve irritable aberrant behavior and also have an improved safety and tolerability profile over atypical antipsychotics in the treatment of fragile X syndrome and/or autism. Baclofen may be used in combination with other medications, such as risperidone, antipsychotics, Group I mGluR antagonists and M1 muscarinic receptor antagonists.

The pharmacokinetics of baclofen and muscarinic M1 antagonists, such as dicylomine, in mice to define systemic exposure can be assessed.

Marble burying behavior in rats is considered to be a model of obsessive-compulsive disorder (OCD) in humans (Matushita, M., et al., *Med. Bull. Fukuoka Univ.* 32:159-165 (2005)). Data described herein show that baclofen inhibits marble-burying behavior.

Subjects with autism can have several symptoms that can range from mild to severe. Such symptoms can include difficulties interacting with others; making friends; communication problems, both with spoken language and nonverbal gestures; insistence on sameness; and some degree of mental retardation or learning disabilities in most, but not all, of affected children. Subjects with a mild autistic spectrum disorder, referred to as Asperger syndrome, can share some of the features of autism, have normal intelligence and can learn to speak at the expected age. Autism is generally diagnosed by observing the behavior of the child and screening tests that assess a number of characteristics and behaviors associated with autism. Subjects with autism can also have, for example, obsessive compulsive behaviors, sleep disorders and/or gastrointestinal disorders.

A broad range of psychiatric drugs are used to treat symptoms and improve behavior in subjects with autism. Antipsychotics are commonly used to treat moderate to severe behavioral problems associated with autism. Risperidone, an atypical antipsychotic that is used to treat aggression, hyperactivity, and other disorders associated with autistic behavior and aberrant behaviors in fragile X syndrome, can be used in combination with the GABA agonists, M1 muscarinic receptor antagonists and Group I mGluR antagonists in the methods described herein. Antagonism of the $5\text{-}HT_{2A}$ and $D_2$ receptors is considered to be crucial for efficacy of the atypical antipsychotics in schizophrenia, with higher occupancy of the $5\text{-}HT_{2A}$ receptor versus $D_2$ being the key to decreased movement side effects. Although all of the atypical antipsychotics share these two pharmacological actions, they differ by having varying activity at other serotonin and dopamine receptors.

Perospirone, an atypical antipsychotic drug approved in Japan for treatment of schizophrenia, has pharmacologic properties that are different from risperidone, and may be useful in the treatment of autism, mental retardation and fragile X syndrome. Perospirone's active metabolite, hydroxyperospirone, has a pharmacologic profile that may be useful to treat anxiety and obsessive-compulsive behavior. For example, hydroxyperospirone achieves relatively high plasma concentrations that are acceptable safety and tolerability levels in humans, and may make a significant contribution to the efficacy observed during treatment with perospirone.

Recent characterization of mutant mice that model human genetic disease and display 'autistic-like' traits provides an opportunity to evaluate pharmacologic interventions on genetically induced and well characterized 'autistic-like' behaviors.

Autism is a disorder characterized by impairments in social interaction and communication, as well as restricted, repetitive and stereotyped patterns of behavior, interests and activities (DSM-IV). The etiology of autism can be medically diagnosed for a less than 10% of individuals and for many of these the diagnosis is attributable to single-gene deficits such as fragile X syndrome, neurofibromatosis or tuberous sclerosis. There is considerable evidence that the remaining cases of "idiopathic" autism represent a largely heritable disorder. Twin studies and data from whole-genome screens suggest that interactions between at least 10 genes predispose to development of autism. Furthermore, it appears that epigenetic and environmental factors contribute to variable expression in those genetically predisposed. The complex interaction of genetic and non-genetic factors in the etiology of "idiopathic" autism has hindered development of representative animal models and development of new pharmaceutical treatments.

In contrast to the complexity of "idiopathic" autism, a number of human monogenic syndromes have a high incidence of autism. Animal models for a number of these human monogenic syndromes are available. These animal models of single gene defects are providing new insights for potential pharmaceutical treatments for diseases such as neurofibromatosis and fragile X syndrome. Fragile X syndrome (Fmr1) knockout mice, which model the single gene defect in the human fragile X syndrome, are used. Some of these mice, as well as some humans with fragile X syndrome, have autistic behaviors.

The methods of the invention can be employed to treat additional conditions that can be associated with autism or fragile X syndrome, for example, Coffin-Lowry syndrome, Cohen syndrome, Duchenne/Becker muscular dystrophies, Neurofibromatosis, Joubert syndrome, Lujan-Fryns syndrome, PTEN mutations, Noonan syndrome, Orstavik syndrome, ARX mutations, CHARGE, Angelman syndrome, Nance-Horan syndrome, Prader-Willi syndrome, Cerebral dysgenesis and Smith-Lemli-Optiz syndrome.

The methods of the invention can be employed to treat pervasive developmental disorders with no identified source and autism and other disorders of brain development.

The methods of the invention can also be employed to treat disorders of brain development including Autism Spectrum Disorders (Pervasive Developmental Disorders), Rett's syndrome, Childhood Disintegrative Disorder, Asperger syndrome and Tuberous Sclerosis.

The methods of the invention can be employed to treat deficits/symptoms, for example, deficits in learning, memory, executive function, attention and/or processing speed. Such deficits can be deficits associated with or observed in subjects with mental retardation, fragile X syndrome, Down's syndrome and autism; and pervasive developmental disorders, including pervasive developmental disorders with no obvious source.

The methods of the invention can be employed to treat neuropsychiatric disorders and anxiety disorders, including anxiety disorders that are associated with or observed in subjects that have mental retardation, autism, Down's syndrome and fragile X syndrome. Such anxiety disorders include, for example, specific phobias, such as phobias of the doctor and dentist; agoraphobia and separation anxiety. Such disorders can also include, for example, bipolar disorders, repetitive and stereotyped behavior, obsessive and compulsive traits/disorders, aggressive behavior, schizophrenia, hyperactivity, pain, itching, sensory hyperarousal, seizures, behavioral problems, sleep disorders (including insomnia, hypersomnia and abnormal behaviors during sleep).

The methods of the invention can also be employed to treat gastrointestinal disorders and metabolic disorders in subjects with mental retardation, fragile X syndrome, Down's syndrome and autism. Autistic behavior (deficits in social interaction, verbal and non-verbal communication, and restricted/ repetitive behaviors or interests) in subjects with autism, mental retardation, fragile X syndrome and Down's syndrome can also be treated by the methods of the invention.

The human administered the GABA agonist, in particular a GABA(B) agonist (e.g., baclofen), can further be administered (e.g., before, concomitantly, sequentially or after) at least one member selected from the group consisting of an antidepressant, a α2-adrenergic agonist, an anticonvulsant, a nicotinic receptor agonist, an endocannabinoid receptor agonist, an anticonvulsant, and anti-psychotic, an AMPA agonist, a M1 muscarinic antagonist and a Group I mGluR antagonist.

The methods of the invention can be employed to treat fragile X-associated tremor/ataxia syndrome (FXTAS) and movement disorders. As discussed above, an excess of about 200 CGG repeats in the 5'-untranslated region of the FMR1 gene results in transcriptional silencing of the FMR1 gene and fragile X syndrome. Subjects with premutation expansions (about 55 to about 200 CGG repeats in the FMR1 gene) are generally unaffected intellectually and may develop FXTAS, which is characterized by progressive cerebellar ataxia, parkinsonism, dementia and autonomic dysfunction (Baba, Y., et al., *Current Opinion in Neurology* 18:393-398 (2005), the teachings of which are hereby incorporated by reference in its entirety).

One of skill in the art would be able to employ well-established criteria to diagnosis a subject that has mental retardation, Down's syndrome, fragile X syndrome and autism and the conditions or deficits described herein. (See, for example, Patzold, L. M., et al., *J. Paediatr. Child Health*, 34:528-533 (1998); Malow, B. A., *Ment. Retard Dev. Disabil. Res. Rev.* 10:122-125 (2004); Robinson, A. M., et al., *Child Care Health Dev.* 30:139-150 (2004); Couturier, J. L., et al., *J. Am. Acad Child Adolesc Psychiatry* 44:815-822 (2005); Kuddo, T., et al., *Curr. Opin. Pediatr.* 15:339-343 (2003); Molloy, C. A., et al., *Autism* 7:165-171 (2003)).

Humans with fragile X syndrome treated by the methods described herein can also have autism.

In an additional embodiment, the invention is a method of treating a human, comprising the step of administering to a human having at least one condition selected from the group consisting of mental retardation, Down's syndrome, fragile X syndrome and autism a composition that includes baclofen, wherein the baclofen is administered to the human at a dose of about 15 mg for days 1, 2 and 3 of treatment, a dose of about 30 mg for days 4, 5 and 6 of treatment, a dose of about 45 mg for days 7, 8 and 9 of treatment, a dose of about 60 mg for days 10, 11 and 12 of treatment and a dose between about 60 mg to about 80 mg per day for the duration of the treatment.

In yet another embodiment, the invention is a method of treating a human, comprising administering to a human having at least one condition selected from the group consisting of mental retardation, Down's syndrome, fragile X syndrome and autism a composition that includes at least about 51 mole percent S-baclofen relative to the total S-baclofen and R-baclofen in the composition administered to the human.

In a further embodiment, the invention is a method of treating a human, comprising administering to a human having at least one condition selected from the group consisting of mental retardation, Down's syndrome, fragile X syndrome and autism a composition that includes at least about 51 mole percent R-baclofen relative to the total R-baclofen and S-baclofen in the composition administered to the human.

The subject treatment by the methods of the invention described herein can be a rodent (e.g., mouse, rat) or a primate (e.g., a monkey, baboon, human). In a particular embodiment, the subject is a human.

In yet another embodiment, the invention is a method of treating a human, comprising the step of administering to a human having at least one condition selected from the group consisting of fragile X syndrome and autism a composition that includes R-baclofen (e.g., at least about 99 mole percent, about 95 mole percent, about 90 mole percent, about 85 mole percent, about 80 mole percent, about 75 mole percent, about 70 mole percent, about 65 mole percent, about 60 mole percent, about 55 mole percent or about 51 mole percent R-baclofen relative to the total R-baclofen and S-baclofen in the composition administered to the human).

In an additional embodiment, the invention is a method of treating a human, comprising the step of administering to a human having at least one condition selected from the group consisting of fragile X syndrome and autism a composition that includes S-baclofen (e.g., at least about 99 mole percent, about 95 mole percent, about 90 mole percent, about 85 mole percent, about 80 mole percent, about 75 mole percent, about 70 mole percent, about 65 mole percent, about 60 mole percent, about 55 mole percent, or about 51 mole percent S-baclofen relative to the total S-baclofen and R-baclofen in the composition administered to the human).

The compounds employed in the methods of the invention can be administered to a subject with (e.g., before, concomitantly, sequentially or after) administration of other compounds that are employed to treat a particular disorder or condition in the subject. For example, the compositions of the invention can be administered with at least one member selected from the group consisting of a Group II mGluR agonist, Group II mGluR agonist, GSK3β antagonists, NAAG peptidase inhibitors, Group I mGluR antagonist, an antidepressant, an anti-psychotic, an α2-adrenergic agonist, an anticonvulsant, a nicotinic receptor agonist, an endocannabinoid receptor antagonist, a M1 muscarinic receptor antagonist, and an AMPA agonist.

Glycogen synthase kinase-3 (GSK3) is an enzyme with a diverse number of actions in intracellular signaling systems, regulating neuronal plasticity, gene expression and cell survival. GSK3β is known to participate in many signaling pathways and cellular activities. GSK3β is a key element of the signaling pathway whereby Group I mGluR signaling regulates dendritic synaptic protein synthesis.

N-Acetyl-1-aspartyl-1-glutamate (NAAG) is one of the three most prevalent neurotransmitters in the mammalian brain. NAAG acts as an agonist at Group II metabotropic glutamate (e.g., mGluR2, mGluR3) receptors on neurons and glia. Specifically, NAAG activation of mGluR receptors reduces cAMP and cGMP levels in neurons and astrocytes. The neuropeptidases glutamate carboxypeptidase II and III (GCPII and III), also known as NAAG peptidases (hereafter "NPs"), are metalloproteases that hydrolyse NAAG to N-acetylaspartate (NAA) and glutamate following the release of NAAG into the synaptic cleft. They are found in limited sites throughout the brain Inhibition of GCPII and III increases NAAG levels, with the consequent activation of presynaptic Group II mGluRs and inhibition of transmitter release, including release of GABA and glutamate.

A Group I mGluR antagonist (mGluR1 and mGluR5) can be administered to the subjects with the compounds employed in the methods of the invention.

mGluRs are a heterogeneous family of glutamate G-protein coupled receptors. mGluRs are classified into three groups. Group I receptors (mGluR1 and mGluR5) can be coupled to stimulation of phospholipase C (PLC) resulting in phosphoinositide (PI) hydrolysis and elevation of intracellular calcium levels, modulation of ion channels (e.g., potassium channels, calcium channels, non-selective cation channels) and N-methyl-D-aspartate (NMDA) receptors. mGluR5 can be present on a postsynaptic neuron. mGluR1 can be present on a presynaptic neuron and/or a postsynaptic neuron.

Group II receptors (mGluR2 and mGluR3) and Group III receptors (mGluRs 4, 6, 7, and 8) inhibit cAMP formation and G-protein-activated inward rectifying potassium channels. Group II mGluRs and Group III mGluRs are negatively coupled to adenylyl cyclase, generally present on presynaptic neurons, but can be present on postsynaptic neurons and function as presynaptic autoreceptors to reduce glutamate release from presynaptic neurons. Activation of Group II mGluRs under very high neuron excitation can dampen further release of neurotransmitters and stimulate the release of neuroprotective growth factors, including trophic factors, from glia.

An antagonist (e.g., a Group I mGluR antagonist, a M1 muscarinic antagonist) is a substance that diminishes or abolishes the effect of a ligand (e.g., glutamate, acetylcholine) that activates its receptor (e.g., mGluR1, mGluR5, M1 muscarinic receptor). The antagonist may act at the level of ligand-receptor interaction, such as by competitively or non-competitively (e.g., allosterically) inhibiting ligand binding. The antagonist (e.g., mGluR1 antagonist, mGluR5 antagonist, M1 muscarinic antagonist) can be, for example, a chemical antagonist or a pharmacokinetic antagonist. The antagonist, for example, may act downstream of the receptor, such as by inhibiting receptor interaction with a G-protein or subsequent cell signaling events associated with G-protein activation, such as activation of PLC, an increase in intracellular calcium, the production of or levels of cAMP or adenyl cyclase and stimulation or modulation of ion channels (e.g., potassium channels, calcium channels).

In one embodiment, the Group I mGluR antagonist is a mGluR5 antagonist. In another embodiment, the Group I mGluR antagonist is an mGluR1 antagonist. Suitable Group I mGluR antagonists for use are described in U.S. Pat. Nos. 6,890,931 and 6,916,821, the teachings of both of which are hereby incorporated by reference in their entirety. Suitable Group I mGluR antagonists can include, for example, (E)-6-methyl-2-styryl-pyridine (SIB 1893), 6-methyl-2-phenylazo)-3-pyridinol, x-methyl-4-carboxyphenylglycine (MCPG) and 2-methyl-6-(phenylthynyl)-pyridine (MPEP).

Exemplary antagonists of mGluR5 for use in the methods of the invention in combination with GABA agonists, in particular GABA(B) agonists (e.g., baclofen), are described in WO 01/66113, WO 01/32632, WO 01/14390, WO 01/08705, WO 01/05963, WO 01/02367, WO 01/02342, WO 01/02340, WO 00/20001, WO 00/73283, WO 00/69816, WO 00/63166, WO 00/26199, WO 00/26198, EP-A-0807621, WO 99/54280, WO 99/44639, WO 99/26927, WO 99/08678, WO 99/02497, WO 98/45270, WO 98/34907, WO 97/48399, WO 97/48400, WO 97/48409, WO 98/53812, WO 96/15100, WO 95/25110, WO 98/06724, WO 96/15099 WO 97/05109, WO 97/05137, U.S. Pat. No. 6,218,385, U.S. Pat. No. 5,672,592, U.S. Pat. No. 5,795,877, U.S. Pat. No. 5,863,536, U.S. Pat. No. 5,880,112, U.S. Pat. No. 5,902,817, all of which are incorporated by reference in their entirety. Different classes of mGluR5 antagonists are described in WO 01/08705, WO 99/44639 and WO 98/34907, the teachings of all of which are hereby incorporated by reference in their entirety.

The antipsychotic compound employed in the methods of the invention can be a typical antipsychotic compound (also referred to as "a typical antipsychotic agent" or a "typical antipsychotic drug"). In another embodiment, the antipsychotic compound is an atypical antipsychotic compound (also referred to as an "atypical antipsychotic agent," an "atypical antipsychotic drug" or a "second generation antipsychotic").

Exemplary atypical antipsychotic compounds for use in the methods of the invention can be at least one member selected from the group consisting of zuclopenthixol, amisulpride, aripiprazole (7-[4-[4-(2,3-dichlorophenyl)-1-piperazinyl]butoxy]-3-4-dihydrocarbostyril), nemonapride, abaperidone (7-[3-[4-(6-fluoro-1,2-benzisoxazol-3-yl)-1-piperidinyl]propoxy]-3-(-hydroxymethyl)-4H-1-benzopyran-4-one, U.S. Pat. No. 5,736,588, the teachings of which are hereby incorporated by reference in its entirety; belaperidone ((1.alpha., 5.alpha., 6.alpha.)-3-[2-[6-(4-fluorophenyl)-3-azabicyclo[-3.2.0]-hept-3-yl]ethyl]-2,4(1H,3H) quinazolinedione, U.S. Pat. No. 5,475,105, the teachings of which are hereby incorporated by reference in its entirety; clozapine (8-chloro-11-(4-methyl-1-piperazinyl)-5H-dibenzo[b,e][1,4]diazepine, U.S. Pat. No. 3,539,573, the teachings of which are hereby incorporated by reference in its entirety issued; iloperidone (1-[4-[3-[4-(6-fluoro-1,2-benzisoxazol-3-yl)-1-piperidinyl]-3-methoxy-phenyl]ethanone; EP-402,644, the teachings of which are hereby incorporated by reference in its entirety; olanzapine (2-methyl-4-(4-methyl-1-piperazinyl)-10H-thieno[2,3-b][1,5]benzodiazepine; U.S. Pat. No. 5,229,382, the teachings of which are hereby incorporated by reference in its entirety; perospirone (cis-2-[4-[4-(1,2-benzisothiazol-3-yl)-1-piperazinyl]butyl]-hexahydro-o-1H-isoindole-1,3(2H)-dione, U.S. Pat. No. 4,745,117, the teachings of which are hereby incorporated by reference in its entirety; risperidone (3-[2-[4-(6-fluoro-1,2-benzisoxazol-3-yl)piperidino]ethyl]-2-methyl-6,7,8,9-tetrahydro-4H-pyrido[1,2-.alpha.]pyrimidin-4-one), U.S. Pat. No. 4,804,663, the teachings of which are hereby incorporated by reference in its entirety; sertindole (1-[2-[4-[5-chloro-1-(4-fluorophenyl-1H-indol-3-yl]-1-piperidinyl]ethyl]imidazolidin-2-one), U.S. Pat. Nos. 4,710,500; 5,112,838; and 5,238,945, the teachings of all of which are hereby incorporated by reference in their entirety; tiospirone (8-[4-[4-(1,2-benzisothiazol-3-yl)-1-piperazinyl]butyl]-8-azaspiro[4-5] decane-7,9-dione), U.S. Pat. No. 4,411,901, the teachings of which are hereby incorporated by reference in its entirety; ziprasidone (5-[2-[4-(1,2-benzoisothiazole-3-yl)-1-piperazinyl]ethyl]-6-chloro-1-,3-dihydro-2-one), U.S. Pat. No. 4,831,031, the teachings of which are hereby incorporated by reference in its entirety; zotepine (2-[(8-chlorodibenzo[b,f] thiepin-10-yl)oxy]-N,N-dimethyl-ethanamine), U.S. Pat. No. 3,704,245, the teachings of which are hereby incorporated by reference in its entirety; quetiapine (5-[2-(4-dibenzo [b,f][1,4]thiazepin-11-yl-1piperazinyl)ethoxy]ethano-1), U.S. Pat. No. 4,879,288, the teachings of which are hereby incorporated by reference in its entirety; and blonanserin (2-(4-ethyl-1-piperazinyl)-4-(4-fluorophenyl)-5,6,7,8,9,10-hexahydro-1-cycloocta[b]pyridine), U.S. Pat. No. 5,021,421, the teachings of which are hereby incorporated by reference in its entirety; 2002/0123490, the teachings of which are hereby incorporated by reference in its entirety).

Antipsychotic agents, including atypical antipsychotic compounds for use in the invention can include, for example, Acetophenazine Maleate; Alentemol Hydrobromide; Alpertine; Azaperone; Batelapine Maleate; Benperidol; Benzindopyrine Hydrochloride; Brofoxine; Bromperidol; Butaclamol Hydrochloride; Butaperazine; Carphenazine Maleate; Carvotroline Hydrochloride; Chlorpromazine; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine; Fluphenazine Decanoate; Fluphenazine Enanthate; Fluphenazine Hydrochloride; Fluspiperone; Fluspirilene; Flutroline; Gevotroline Hydrochloride; Halopemide; Haloperidol; Iloperidone; Imidoline Hydrochloride; Lenperone; Loxapine; Mazapertine Succinate; Mesoridazine; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palmnitate; Piquindone Hydrochloride; Prochlorperazine Edisylate; Prochlorperazine Maleate; Promazine Hydrochloride; Quetiapine; Remoxipride; Quetiapine Remoxipride Hydrochloride; Risperidone; Risperadone Rimcazole Hydrochloride; Seperidol Hydrochloride; Sertindole; Setoperone; Spiperone; Sulpiride; Thioridazine; Thiothixene; Thorazine; Tioperidone Hydrochloride; Tiospirone Hydrochloride; Trifluoperazine Hydrochloride; Trifluperidol; Triflupromazine; Ziprasidone Hydrochloride, analogs, derivative and combinations thereof (see, for example, U.S. Patent Application Nos: 20040019030 and 2002/0123490, the teachings of both of which are hereby incorporated by reference in their entirety).

Antipsychotic compounds can have adverse side effects including, for example, central nervous system depression, weight gain, sexual dysfunction, adverse effects on mood, anticholinergic side effects (cognitive impairment, reduced memory capacity, confusion, delirium, dry mouth, blurred vision, worsening of glaucoma, constipation, urinary retention, tachycardia), weight gain, diabetes mellitus, prolactin elevation, QTC prolongation, sedation, motor side effects such as extrapyramidal symptoms (EPS), dystonia, drug-induced parkinsonism, akathisia and potentially persistent drug-induced movement disorders and motor side effects such as tardive dyskinesia (see, for example, U.S. Publication No: 2003/0008897, the teachings of which are hereby incorporated by reference in its entirety). These adverse side effects can reduce patient compliance and lead to relapses.

Atypical antipsychotic compounds can reduce psychotic symptoms with fewer side effects (e.g., extrapyramidal side effects, rigidity, tremor, akathisia, cognitive impairment) than typical antipsychotics (see, for example, Citrome, L., et al., Postgraduate Medicine 116: (2004)). In addition, atypical antipsychotics can also reduce aggression, repetitive behaviors, hallucinations, delusions, amotivation and emotional withdrawal. However, not all side effects (e.g., weight gain, impaired glucose tolerance/lipid abnormalities, impaired social interaction) are eliminated by the use of atypical antipsychotics. Group I mGluR antagonist have been shown to reduce weight gain and decrease appetite. Combinations of Group I mGluR antagonists and antipsychotics in the methods of the invention described herein, in particular atypical antipsychotics, may diminish or reduce the side effects of antipsychotic compounds y reducing the dosage required and increase compliance to thereby treat subjects having conditions such as mental retardation, fragile X syndrome, Down's syndrome, autism, pervasive developmental disorders, including pervasive developmental disorders with no obvious source.

The methods of the invention can further include the step of administering at least one member selected from the group consisting of a nicotinic receptor agonist, an endocannabinoid receptor antagonist, an AMPA agonist, an antidepressant, an antipsychotic, an α2-adrenergic agonist, an anticonvulsant, a nicotinic receptor agonist, an endocannabinoid receptor antagonist and an AMPA agonist, which can be administered before, during or after administration of the Group I mGluR antagonist, M1 muscarinic receptor antagonist and/or the GABA(B) receptor agonist, to the human.

In an embodiment, the GABA receptor agonist is administered (e.g., before, concomitantly, sequentially or after) the M1 muscarinic receptor agonist.

In yet another embodiment, the invention method of treating a subject, comprising the step of administering to a subject having at least one condition selected from the group consisting of mental retardation, Down's syndrome, fragile X syndrome and autism a composition that includes at least one M1 muscarinic antagonist (also referred to herein as "M1 muscarinic receptor antagonist").

The muscarinic acetylcholine (mACh) receptor family consists of five members (M1, M2, M3, M4 and M5) and belongs to the G protein-coupled receptor (GPCR) superfamily. A characteristic of GPCRs is that ligand binding, the initial step in receptor signaling, elicits a conformational change in the receptor, leading to the activation of one or more heterotrimeric G proteins. Mucarinic M1 receptors may preferentially couple to the activation of PLC by pertussins toxin (PTx)-insensitive G proteins of the Gq family (Akam, E. C., et al., *British J. Pharmacology* 132:950-958 (2001)).

Each muscarinic acetylcholine receptor shares common features including specificity of binding for the agonists acetylcholine and carbamylcholine and the classical antagonists atropine and quinuclidinyl benzilate. Each receptor subtype couples to a second messenger system through an intervening G-protein. M1, M3 and M5 receptors stimulate phosphoinositide metabolism whereas M2 and M4 receptors inhibit adenylate cyclase. The tissue distribution differs for each subtype. M1 receptors are found in the forebrain, especially in the hippocampus and cerebral cortex. M2 receptors are found in the heart and brainstem while M3 receptors are found in smooth muscle, exocrine glands and the cerebral cortex. M4 receptors are found in the neostriatum and M5 receptor mRNA is found in the substantia nigra, suggesting that M5 receptors may regulate dopamine release at terminals within the striatum.

Activity of Gq-coupled, M1 muscarinic (also referred to herein as "muscarinic M1") acetylcholine receptors can regulate hippocampal-dependent learning and memory consolidation. M1 muscarinic acetylcholine receptors (mAChRs), the primary Gq-coupled mAChRs in hippocampus, contribute to hippocampal-dependent memory.

M1 muscarinic antagonists, such as scopolamine and atropine, can abolish or diminish the action of signal transduction pathways that are mediated by M1 muscaranic receptors. Scopolamine and atropine are alkaloids (natural, nitrogenous organic bases, usually containing tertiary amines) from the plant *Atropa belladonna*. The presence of an N-methyl group on atropine or scopolamine changes the activity of the ligand, possibly by preventing a close interaction between the ligand and the membrane or lipophilic sites on the receptor. The methyl group may prevent the penetration into the brain.

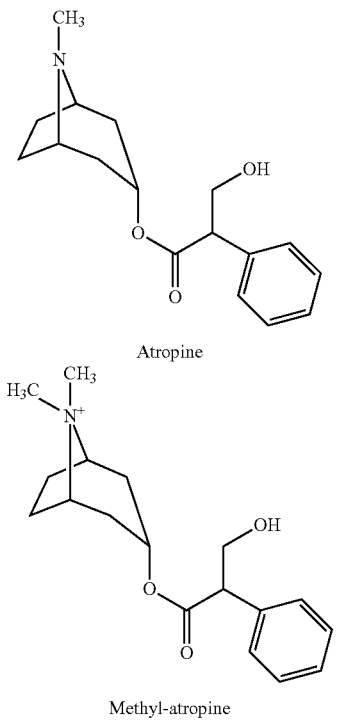

Atropine

Methyl-atropine

Exemplary M1 muscarinic receptor antagonists (also referred to herein as "M1 muscarinic antagonists" or muscarinic M1 antagonists") for use in the methods of the invention, in combination with a GABA agonist, in particular, a GABA (B) agonist, can include the following:

Telenzepine is a racemic, analog that is more potent than Pirenzepine (Merck, Gastrozepen). Pirenzepine does not cross the blood brain barrier, but telenzepine may and may have reactive metabolites. The muscarinic M1 receptor antagonist (+/−)-telenzepine (about 3 mg orally at about 6 p.m. for about 5 days) has been used to treat chronic obstructive pulmonary disease (COPD). The results indicate that short-term treatment with telenzepine does not improve airway function in COPD patients, at least after administration by the oral route.

Trihexyphenidyl (Artane) is an antiparkinson agent of the antimuscarinic class of agents and is chemically a tertiary amine. The drug is available as the hydrochloride salt.

Benztropine (Cogentin) (Merck) is an anticholinergenic and an antihistamine. It has been used in patients with schizophrenia to reduce the side effects of antipsychotic treatment, such as parkinsonism and akathisia. Benztropine is also a second-line drug for the treatment of Parkinson's disease. It improves tremor but not rigidity or bradykinesia. Benztropine is also sometimes used for the treatment of dystonia, a rare disorder that causes abnormal muscle contraction, resulting in twisting postures of limbs, trunk, or face.

Dicyclomine (Bentyl) has been used to treat intestinal hypermotility, the symptoms of Irritable Bowel Syndrome (also known as spastic colon). It relieves muscle spasms in the gastrointestinal tract by blocking the activity of a certain natural substance in the body. It is a smooth muscle relaxer. Bentyl is also referred to as Byclomine, Dibent, Di-Spaz, Dilomine, Bentylol (Hoechst Marion Roussel), Formulex (ICN) and Lomine (Riva).

Biperiden (1-(5-bicyclo[2.2.1]hept-2-enyl)-1-phenyl-3-(1-piperidyl)propan-1-ol) is an antiparkinsonian agent of the anticholinergic type and is also referred to as Akineton® (BASF/Knoll Pharma).

Procyclidine (1-cyclohexyl-1-phenyl-3-pyrrolidin-1-yl-propan-1-ol hydrochloride) has been used to treat schizophrenia to reduce the side effects of antipsychotic treatment, such as parkinsonism and akathisia. Procyclidine is also a second-line drug for the treatment of Parkinson's disease and can improve tremors, but not rigidity or bradykinesia. Procyclidine may be employed to treat dystonia (but not tardive dyskinesia), a rare disorder that causes abnormal muscle contraction, resulting in twisting postures of limbs, trunk, or face.

Scopolamine ((−)-(S)-3-Hydroxy-2-phenyl-propionic acid (1R,2R,4S,7S,9S)-9-methyl-3-oxa-9-aza-tricyclo[3.3.1.02,4]non-7-yl ester) acts as a competitive antagonist at specific muscarinic acetylcholine receptors (the M1 receptor). Scopolamine is classified as an anticholinergic, or, more specifically, as an anti-muscarinic drug.

The quaternary muscarinic antagonist ipratroprium and the long-lasting tiotropium can also be employed.

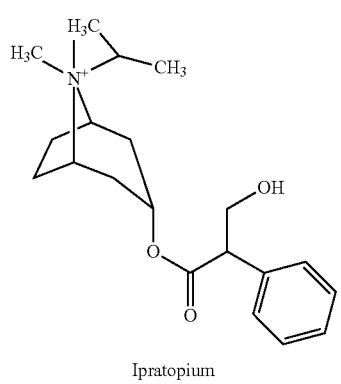

Ipratopium

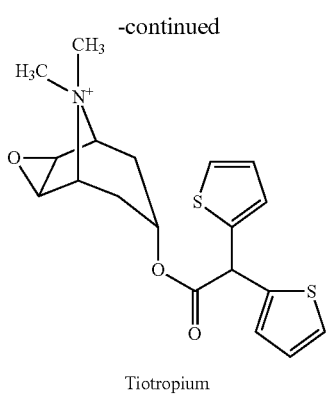

Tiotropium

Enantomerically (+, −; R, S; d, 1) enriched compositions (e.g., about 99 mole percent, about 98 mole percent, about 95 mole percent, about 90 mole percent, about 85 mole percent, about 80 mole percent, about 75 mole percent, about 70 mole percent, about 65 mole percent, about 60 mole percent, about 55 mole percent, about 51 mole percent of one enantiomer in the composition relative to the total of both of the enantiomers in the composition) of the M1 muscarinic antagonists can be employed in the methods described herein.

The methods of the invention can further include the step of administering a stimulant to the subject. "Stimulant," as used herein, refers to any compound that promotes or increases wakefulness, alertness, physical activity, enhances cognition, enhances learning or diminishes fatigue. Stimulants for use in the invention can include amantadine, bupropion, atomoxetine, modafinil, caffeine, methylphenidate, nicotine, pseudoephedrine, and amphetamine, or metabolites, isomers (e.g., d, l, R, S) or derivatives thereof. The stimulant used in the methods described herein can antagonize adenosine receptor, inhibit dopamine reuptake, inhibit norepinephrine reuptake, antagonize H3 receptor, promote dopamine release, inhibit monoamine oxidase in the nervous system (the central nervous system, peripheral nervous system, and autonomic nervous system) or any combinations thereof.

The compounds employed in the methods of the invention can be administered to a subject with (e.g., before, concomitantly, sequentially or after) administration of other compounds that are employed to treat a particular disorder or condition in the subject. For example, the compositions of the invention can be administered with at least one member selected from the group consisting of an antidepressant, a Group I mGluR antagonist, a muscarinic M1 antagonist, an anti-psychotic, an α2-adrenergic agonist and an anticonvulsant.

The identification of appropriate compounds, such as antidepressants, antipsychotics, α2-adrenergic agonists, anticonvulsants, a nicotinic receptor agonist, an endocannabinoid receptor antagonist and AMPA agonists, for use in the methods of the invention would be known to one skilled in the art (see, for example, Beryy-Kravis, E., et al., Mental Retardation and Developmental Disabilities 10: 42-48 (2004), the teachings of which are hereby incorporated by reference in its entirety).

The compounds employed in the methods of the invention can be administered to the subject acutely (briefly or short-term) or chronically (prolonged or long-term). For example, subjects can be administered the compounds for days (1-7), months (1, 2, 3, 4, 5, 6, 7, 8, 9, 10, 11, 12), years (1, 2, 3, 4, 5, 6, 7, 8, 9, 10, 11, 12) or for life.

Subjects treated by the methods of the invention can have at least one condition selected from the group consisting of a sensory hyperarousal disorder, an anxiety disorder, a seizure disorder, a gastrointestinal disorder, a sleep disorder, aggressive or aberrant behavior and an impaired cognitive function.

Subjects treated by the methods of the invention can also have at least one condition selected from the group consisting of a social interaction abnormality, limited interests and repertoire of behaviors and a social avoidance condition.

Subjects (e.g., humans, also referred to herein as "patients") treated by the methods of the invention can have a cognitive impairment, such as an impairment in reaction time, eye tracking, motor coordination, gait, oral-motor function, communication, learning, attention, executive function, reaction time, learning, information processing, conceptualization, problem solving, verbal fluency or memory (e.g., memory consolidation, short-term memory, working memory, long-term memory, declarative memory or procedural memory).

Impairment in a cognitive function treated by the methods described herein can be an impairment in attention, which is the capacity or process of selecting out of the totality of available sensory or affective stimuli, those stimuli that are most appropriate or desirable for focus at a given time (Kinchla, R. A., et al., *Annu. Rev. Psychol.* 43:711-742 (1992)). The impairment in a cognitive process can be an impairment in executive function, which are neuropsychological functions such as decision making, planning, initiative, assigning priority, sequencing, motor control, emotional regulation, inhibition, problem solving, planning, impulse control, establishing goals, monitoring results of action and self-correcting (Elliott, R., *Br. Med. Bull.* 65:49-59 (2003)). The cognitive impairment can be an impairment in alertness, wakefulness, arousal, vigilance, and reaction time information processing, conceptualization, problem solving and/or verbal fluency. One of skill in the art would be capable of identifying and evaluating the impairment in a cognitive function in the individual.

An "effective amount," also referred to herein as a "therapeutically effective amount," when referring to the amount of a compound or composition (e.g., baclofen, a M1 muscarinic receptor antagonist) is defined as that amount, or dose, of a compound or composition that, when administered to a subject, is sufficient for therapeutic efficacy (e.g., an amount sufficient decrease to exhibit a clinical improvement in a behavior or mental cognitive test score; alleviate sensory hyperarousal disorder, an anxiety disorder, a seizure disorder, a gastrointestinal disorder, a sleep disorder, prevent weight gain, decrease obsessive compulsive tendencies and manners).

The methods of the present invention can be accomplished by the administration of the compounds of the invention (e.g., compositions including baclofen) by enteral or parenteral means. The route of administration can be by oral ingestion (e.g., tablet, capsule form) or intramuscular injection of the compound. Other routes of administration can include intravenous, intraarterial, intraperitoneal, or subcutaneous routes, nasal administration, suppositories and transdermal patches.

In an embodiment, the compounds (e.g., baclofen, Group I mGluR antagonists, M1 muscarinic receptor antagonists) employed in the methods of the invention can be administered in a dose of between about 0.01 mg/kg to about 0.1 mg/kg; about 0.001 mg/kg to about 0.01 mg/kg; about 0.001 to about 0.05 mg/kg; about 0.1 mg/kg to about 1 mg/kg body weight; about 1 mg/kg to about 5 mg/kg body weight; or between about 5 mg/kg to about 15 mg/kg body weight.

The compounds can be administered in doses of about 0.1 mg, about 1 mg, about 2 mg, about 2.5 mg, about 5 mg, about 10 mg, about 15 mg, about 20 mg, about 25 mg, about 30 mg, about 40 mg, about 45 mg, about 50 mg, about 60 mg, about 80 mg, about 100 mg, about 200 mg, about 250 mg, about 300 mg, about 350 mg, about 400 mg, about 500 mg, about 600 mg, about 700 mg, about 900 mg, about 1000 mg, about 1200 mg, about 1400 mg, about 1600 mg or about 2000 mg, or any combination thereof. The compounds can be administered once a day or multiple (e.g., two, three, four, five) times per day.

In yet another embodiment, the subject is administered the compounds employed in the methods of the invention at about 1 mg BID (twice a day), about 2 mg BID, about 3 mg BID, about 5 mg BID, about 10 mg BID and about 10 mg TID (three times a day).

In another embodiment, the compounds employed in the methods of the invention can be administered at a dosing regimen that includes progressive or escalating increases in the compound over time of treatment. For example, a subject can be treated with baclofen (e.g., R-baclofen, such as between about 20 to about 40 mg per day) at a dose of about 2 mg/day at days 1, 2, 3 of treatment; about 4 mg/day at days 4, 5, 6 of treatment; about 6 mg/day at days 7, 8, 9 of treatment; about 20 mg/day at days 13, 14, 15 of treatment and about 30 mg/day at days 16, 17 and 18 of treatment.

The compounds of the invention can be administered to the human in a selected dose (e.g., about 10 mg dose taken 3 times a day or about 15 mg dose given as three doses each of which is about 5 mg) while monitoring improvements in the human (e.g., cognition, behavior). If the human does not exhibit any improvement, the compositions employed in the methods can be increased, decreased or stopped until a beneficial effect is observed. For example, if treatment began with three (3) doses of about 10 mg daily and the human subsequently exhibited no apparent improvement, the dose could be increased to three (3) doses of about 15 mg a day, decreased to two (2) doses of about 10 mg a day or treatment could be halted for a single dose, a number of days or weeks and subsequently commenced following the "mini-drug holiday."

"Mini-drug holiday," as used herein, refers to removal of the human from treatment or a decrease in the dose of the compound, followed by re-introduction of the treatment, at a dose equivalent to, below or in excess of the dose the human received prior to the mini-drug holiday.

In yet another embodiment, the invention is a method of treating a human, comprising the step of administering to a human having at least one condition selected from the group consisting of mental retardation, Down's syndrome, fragile X syndrome and autism a composition that includes baclofen, wherein the baclofen is administered to the human at a dose of about 2 mg per day for days 1, 2 and 3 of treatment, a dose of about 4 mg per day for days 4, 5 and 6 of treatment, a dose of about 6 mg per day for days 7, 8 and 9 of treatment, a dose of about 10 mg per day for days 10, 11 and 12 of treatment, a dose of about 20 mg per day for days 13, 14 and 15 of treatment, a dose of about 30 mg per day for days 16, 17 and 18 of treatment and a dose between about 15 mg to about 80 mg per day for the duration of the treatment or between about 30 mg to about 80 mg per day for the duration of the treatment.

In an additional embodiment, the invention is a method of treating a human, comprising the step of administering to a human having at least one condition selected from the group consisting of mental retardation, Down's syndrome, fragile X syndrome and autism a composition that includes baclofen, wherein the baclofen is administered to the human at a dosing regimen of at least one member selected from the group consisting of about 1 mg twice a day, about 2 mg twice a day, about 3 mg twice a day, about 5 mg twice a day, about 10 mg twice a day and about 10 mg three times a day.

One skilled in the art can adjust doses of compounds for use in the methods. A suitable dose of a compound (e.g., a GABA (B) agonist, such as baclofen; M1 muscarinic receptor antagonist) for use in a subject can be a titrated dose. For example, the subject would initially receive a low dose, doses would be increased if the low dose was not effective. Doses could be increased about every 3-7 days of treatment, with adjustments as necessary based on side-effects. The doses can be titrated until the maximal tolerated dose or maximally effective dose is determined. Subjects can be maintained at the maximally effective or maximally tolerated dose.

In one embodiment, the baclofen administered to the human is a racemic mixture (50 mole percent R-baclofen and 50 mole percent S-baclofen). In another embodiment, the baclofen administered to the human is enriched for one enantiomer of baclofen.

The enatomerically enriched baclofen can include a composition that is at least about 51 mole percent, at least about 55 mole percent, at least about 60 mole percent, at least about 65 mole percent, at least about 70 mole percent, at least about 75 mole percent, at least about 80 mole percent, at least about 85 mole percent, at least about 90 mole percent, at least about 95 mole percent, at least about 98 mole percent, at least about 99 mole percent or 100 mole percent R-baclofen relative to the total R-baclofen and S-baclofen in the composition administered to the human.

Alternatively, the enatomerically enriched baclofen can include a composition that is at least about 51 mole percent, at least about 55 mole percent, at least about 60 mole percent, at least about 65 mole percent, at least about 70 mole percent, at least about 75 mole percent, at least about 80 mole percent, at least about 85 mole percent, at least about 90 mole percent, at least about 95 mole percent, at least about 98 mole percent, at least about 99 mole percent or 100 mole percent S-baclofen relative to the total S-baclofen and R-baclofen in the composition administered to the human.

The compounds employed in the methods of the invention can be administered alone or can be coadministered to the patient. Coadministration is meant to include simultaneous or sequential administration of one or more of the compounds (e.g., baclofen and a M1 muscarinic receptor antagonist) employed in the methods of the invention individually or in combination. The mode of administration can be conducted sufficiently close in time to each other so that the effects on the subject are maximal. It is also envisioned that multiple routes of administration (e.g., intramuscular, oral, intranasal, inhalation, topical, transdermal) can be used to administer the compounds employed in the methods of the invention.

The compounds employed in the methods of the invention can be administered alone or as admixtures with conventional excipients, for example, pharmaceutically, or physiologically, acceptable organic, or inorganic carrier substances suitable for enteral or parenteral application which do not deleteriously react with the compound(s) administered to the subject. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrrolidine. Such preparations can be sterilized and, if desired, mixed with auxillary agents such as lubricants, preservatives, stabilizers, wetting agents, emulsifiers, salts for influencing osmotic pressure, buffers, coloring, and/or aromatic substances and the like which do not deleteriously react with the compounds employed in the methods of the invention. The preparations can also be combined, when desired, with other active substances to reduce metabolic degradation. A preferred method of administration of the compounds employed in the methods of the invention can be oral administration, such as a tablet.

The compounds employed in the methods of the invention, alone, or when combined with an admixture, can be administered in a single or in more than one dose over a period of time to confer the desired effect (e.g., alleviate symptoms of autism, improve sleep patterns, decrease sensory hyperarousal disorder, alleviate an anxiety disorder, a seizure disorder, a gastrointestinal disorder, an impaired cognitive function, weight gain).

When parenteral application is needed or desired, particularly suitable admixtures for the compounds employed in the methods of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds for use in the methods of the invention can also be incorporated into liposomes or administered by transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309 the teachings of which are hereby incorporated by reference.

The dosage and frequency (single or multiple doses) administered to an individual can vary depending upon a variety of factors, including the duration of condition of the subject (e.g., sensory hyperarousal disorder, anxiety disorder, seizure disorder, gastrointestinal disorder, sleep disorder, an impaired cognitive function, weight gain, obsessive compulsive behaviors); the route of administration of the compound; size, age, sex, health, body weight, body mass index, and diet of the recipient; nature and extent of symptoms of the disorder being treated (e.g., sensory hyperarousal disorder, anxiety disorder, seizure disorder, gastrointestinal disorder, sleep disorder, impaired cognitive function), kind of concurrent treatment (e.g., behavioral modification, anti-depressant medications, $\alpha$2-adrenergic agonists, anticonvulsants, a nicotinic receptor agonist, an endocannabinoid receptor antagonist, AMPA agonists, anti-psychotics), complications from, for example, a sensory hyperarousal disorder, anxiety disorder, seizure disorder, gastrointestinal disorder, sleep disorder or impaired cognitive function; or other health-related problems. Other therapeutic regimens or agents can be used in conjunction with the methods of the present invention. For example, the administration of the compounds employed in the methods of the invention can be accompanied by behavioral modifications, anti-depressant medications and anti-psychotic medications. Adjustment and manipulation of established dosages (e.g., frequency and duration) are well within the ability of those skilled in the art.

An additional embodiment of the invention is the use of the compositions and compounds (e.g., baclofen, M1 muscarinic receptor agonist, Group I mGluR antagonists) for the manufacture of a medicament to treat subjects (e.g., humans) having the conditions described herein (e.g., fragile X syndrome, autism).

A further embodiment of the invention is a pharmaceutical composition that includes the compositions and compounds described herein (e.g., baclofen, M1 muscarinic receptor antagonists, Group I mGluR antagonists) to treat subjects having the conditions described herein (e.g., fragile X syndrome, autism).

A description of example embodiments of the invention follows.

The teachings of all patents, published applications and references cited herein are incorporated by reference in their entirety.

EXEMPLIFICATION

Example 1

Treatment of Autism with Baclofen

A 23 year old female with autism spectrum disorder (height 61", weight 170 lbs) was hospitalized and being preparing for port-a-catheter placement to begin TPN for an undetermined period of time to allow total gut rest. Baclofen was prescribed 5 mg tid (three times daily) to improve bowel motility. Within about 24 hours abdominal pain appeared to be resolved and GI motility became functional, allowing oral feeding. Over the next several days and weeks improvements were noted in cognitive and behavioral domains that had been unchanged for over 10 years.

For example, improvements with social interaction as evidenced by
- a) Increased interest and response to spoken language
- b) Increased spontaneous attempts to interact
- c) Increased joint attention and eye contact;
  improvements in motor coordination as evidenced by
- a) greatly improved oral motor
- b) improved motor planning
- c) improved gait;
  improvements in communication as evidenced by
- a) immediate and appropriate responses to spoken language (receptive language)
- b) increase in verbal language ("No" "OK" "go") and attempts at word approximations
- c) increased spontaneous use of augmentative communication device;
  dramatic improvements in mood and affect "looks comfortable, calm and happy";
  increased interest and motivation to work on cognitive/educational activities;
  greatly increased physical stamina and energy;
  increased repertoire of age appropriate behavior and interests.

After about 3 weeks of baclofen (about 5 mg tid), the beneficial effects began to wane. At that time the dose was increased to about 10 mg tid, but the increase in dose did not produce the beneficial effects noted above. A single dose of about 15 mg produced the typical side effects of sedation. An alternative dosing regimen included omission of the evening dose for one day (e.g., a mini-drug holiday) followed by resumption of the original dose (about 5 mg tid) the next day, which resulted in beneficial effects on cognitive and behavioral domains, as described above. Efficacy has been observed for over about 11 weeks at present at a dose of about 10 mg bid (twice a day). When positive effects begin to wane, a single dose is omitted and full efficacy is again observed. During the first two months it was necessary to skip a dose about once every 5-7 days to maintain full efficacy, more recently this interval has increased to once every 10-14 days.

The improvements observed were in domains that had been unchanged and stable for over ten years (e.g., communication, verbalization, joint attention, socialization, coordination), maximal benefits occurred at doses lower than those typically found effective for treating gastrointestinal spasticity (the approved indication), improvements were correlated with a specific dose range, and tolerance to beneficial effects was not rescued by increasing the dose but was repeatedly rescued by skipping a single dose.

This 23 year old female was on the following medications at the time of initiation of baclofen:
175 mg topamax: pain and history of 4 gran mal seizures (none since 2002);
30 mg prevacid bid;
150 mg zantac tid;
8 mg zofran every 8 hours to treat chronic vomiting;
500 mg Philips magnesium tid to treat constipation;
dulcolax as needed for constipation;
100 mg tramadol as needed (every 6-8 hours); and
oxycodone for breakthrough pain This 23 year old female was given a trial of amitryptiline for 3 days in the hospital prior to baclofen treatment with no effect. The tramadol and oxycodone were discontinued when the baclofen was started. Over the past few weeks she was weaned off many of the above medications. Her current medications are:
baclofen 20 mg (10 mg twice a day);
topamax 125 mg; and
zantac 150 mg.

Example 2

Treatment of Autism with Baclofen

A 12 year old male with autism spectrum disorder (height=54", weight=64 lbs) was treated with baclofen. Baclofen (about 5 mg bid) was initially administered with baclofen in an attempt to reduce gastroesophageal reflux symptoms. Over the next several days and weeks improvements were noted in several cognitive and behavioral domains such as increased interest and response to spoken language and attempts to communicate verbally. Dramatic improvements in mood and affect such as "looks comfortable, calm and happy" were also noted. Increased alertness, interest and motivation to work on cognitive/educational activities with school instructors were also noted. School personnel record behavior on a daily basis, are not informed regarding changes in drug treatment and did not know that baclofen had been prescribed for this subject. Daily scores were averaged over the five weeks after initiating baclofen therapy and compared to the average scores for the five weeks immediately preceding initiation of baclofen therapy. Significant improvements following initiation of baclofen were noted in the following domains:
Episodes of scratching, hitting and kicking others decreased from an average of 17+2 (mean+SE) to 6+1 episodes a day episodes a day.
Episodes of hand biting or hitting of the head decreased to from an average of 15+2 to 6+1 episodes a day.
Episodes of eye diversion decreased from an average of 10+2 to 5+2 episodes a day.
These benefits have been maintained for 5 weeks on stable dosing at 5 mg bid.
Concomitant medications at the time of initiation of baclofen:
Tegretol 800 mg/day for history of 4 gran mal seizures
Prevacid 30 mg bid
Lamotrigine 25 mg/day
Singulair 5 mg/day
Carafate 1 gm bid

Example 3

Treatment of Autism with Baclofen

A 9 year old male with autism spectrum disorder (height=46", weight=47 lbs) was treated with baclofen. Baclofen (5 mg bid) was initiated in an attempt to reduce gastroesophageal reflux symptoms. Over the next several days and weeks improvements were noted in cognitive and behavioral domains, such as increased interest and response to spoken language and spontaneous attempts to communicate. Parents also noted an improvement in sleep patterns, mood and affect. Increased alertness, interest and motivation to work on cognitive/educational activities were noted by school personnel. School personnel record behavior on a daily basis, are not informed regarding changes in drug treatment and did not know that baclofen had been prescribed for this subject. Daily scores were averaged over the five weeks after initiating baclofen therapy and compared to the average scores for the five weeks immediately preceding initiation of baclofen therapy. Improvements were noted in the frequency of startle/tremor activity, which is thought to reflect brief (approximately 2 second duration) seizure activity in this subject. After initiation of baclofen treatment, episodes of startle tremor decreased from an average of 66+24 (mean±SE) to 16+5 episodes a day. Similarly, the incidence of spontaneous attempts to communicate increased from an average of 11+1 to 21+2 episodes a day.

These benefits have been maintained for 5 weeks on stable dosing at 5 mg bid.

Concommitant medications at the time of initiation of baclofen:

Tegretol 800 mg/day for history of seizures
Prevacid 30 mg bid
Lamotrigine 50 mg/day
Singulair 10 mg/day

Example 4

Autism Spectrum Disorder with Baclofen

Racemic baclofen was administered to treat twenty one (21) subjects (12 males and 9 females) with autism spectrum disorder (see Table 1). The subjects had serious behavioral problems that were not controlled with a variety of medications including antiepileptics (N=14), antipsychotics (N=8) and antidepressants (N=6). Doses of baclofen administered to the subjects were titrated on a weekly basis from about 2.5 mg twice a day (BID) to a maximum of about 15 mg three times a day (TID), with a maximum duration of treatment of about 8.5 months.

The clinician rated overall impression of improvement with baclofen treatment on a seven category scale ranging from "much worse," "worse," "slightly worse," "no change," "slightly better," "better" or "much better." Subjects undergoing baclofen treatment were considered to have improved if the clinician rating was either "much better" or "better." Likewise, baclofen was considered to not improve the condition of the subject if the clinician rating was "slightly worse," "no change" or "slightly better." If a subject was worse on baclofen treatment, the clinician rating would be "worse" or "much worse."

Eight (8) of the 21 subjects demonstrated improvement in presenting symptoms including less irritability/aggression, better communication or improved social interaction. Other areas of improvement included increased class participation and decreased hyperactivity. Eleven (11) subjects did not improve and two (2) subjects worsened. Eight (8) subjects did not continue on baclofen treatment. These included 2 who did not improve, 1 patient who improved but did not continue treatment, 3 patients who stopped for unrelated reasons, and 2 who had adverse side effects that were considered related to initiation of baclofen treatment (drowsiness in one and hyperactivity in the other). Other adverse effects included difficulty sleeping, otitis, increased gastrointestinal discomfort/loose stools and increase in finger stims.

Racemic baclofen has been used to treat spasticity and has a well-defined safety profile in adults and children. There is no rationale for prescribing baclofen to children with disorders of brain development. In the patients with fragile X syndrome, doses of racemic baclofen were titrated from a starting dose of about 2.5 or about 5 mg BID to a maximum of about 20 mg TID, with a maximum duration of 4 months. Two of five patients demonstrated improvement in behavior, including less irritability, aggression and agitation, two are still undergoing titration, and treatment was discontinued in one subject who developed sleepiness and irritability when the dose was increased to about 20 mg/day. Other areas of improvement included increased class participation and decreased hyperactivity. Of note, all fragile X syndrome patients (Example 5) were receiving psychoactive drugs and four of five were receiving concurrent treatment with atypical antipsychotics. In the patients with idiopathic autism, doses were titrated from about 2.5, 5 or 10 mg BID to a maximum of about 15 mg TID, with a maximum duration of about 8.5 months. Eight of the 21 patients demonstrated improvement in presenting symptoms, including less irritability/aggression, better communication/social interaction, and decreased frequency and severity of gastrointestinal symptoms. Other areas of improvement included increased class participation and decreased hyperactivity. Baclofen treatment was discontinued in eight patients including one who improved, five who did not improve and two patients who worsened (increased hyperactivity in both). Of note, these patients were commonly receiving concurrent treatment with psychoactive drugs including antiepileptics (N=14), antipsychotics (N=8) and antidepressants (N=6). The overall impression was that baclofen was particularly useful for treatment of irritable and aggressive behavior.

TABLE 1

Baclofen Treatment in Autism Spectrum Disorder Patients

| Age (Yrs) | Weight (kg) | Sex | Concomitant Conditions | Concomitant Medications | Reason for Baclofen Treatment | Maximum Total Daily Dose (mg) | Treatment Duration (months) |
|---|---|---|---|---|---|---|---|
| 14 | — | F | None | Risperdal, fluoxitine, valproic acid | agitation | 20 | 7.5 |

TABLE 1-continued

Baclofen Treatment in Autism Spectrum Disorder Patients

| | | | | | | | |
|---|---|---|---|---|---|---|---|
| 29 | — | M | None | fluoxetine, Abilify, Remeron | compulsions | 40 | 4 |
| 37 | — | F | Bipolar mood disorder | Risperdal, Synthroid, Temazepam, baclofen, benztropine | agitation, dystonia | 20 | 1 |
| 15 | 59.1 | F | Mental retardation | Trileptol, Seroquel, Lexapro | aggression, rigidity, insistence on sameness | 45 | 3.5 |
| 14 | 50 | F | Mental retardation | Lithobid, Lithium carbonate, Seroquel | aggression, irritability, constant movement | 20 | 5.5 |
| 4 | 22 | M | Lactose intolerance, chronic diarrhea, suspected metabolic problem, increased illness/fevers in winter (symptoms of autism decreased during these periods), history of regression 20 mos. | Vitamin cocktail, Pepcid, Vit. B6, A, D, Nystatin, Zinc, Colostrum Gold | gastrointestinal dysfunction, behavioral symptoms | 5 | 1 |
| 13 | 65.2 | M | GI tract issues, undefined metabolic issues, processing problems-needs augmentative communication device for language | Vitamin cocktail (CO QID, B1, B2, E) | restrictive, repetitive behaviors, decreased energy level | 10 | 4.5 |
| 12 | 50.1 | F | Seizures, reflux, unspecified metabolic disorder, psoriasis, anxiety, PICA, weight loss, dysphagia | Paxil, Donovex ointment, omeprazole, Atarax, Depakote | GI distress, behavioral symptoms | 5 | >1 |
| 9 | 50.7 | M | esophagitis, allergy, questionable metabolic disorder, distractibility, rash, sleep problems, gluten and casein-free diet | Singulair, Prevacid, Carnitine, Vitamin cocktail (CO, Q10, E, C, B1, B2) | GI tract issues, sleep problems, behavior | 20 | 1 |
| 7 | 29.1 | M | reflux, sour stomach, no appetite, suspected metabolic disorder, attention problems, anxiety, depression, chronic skin eruptions on face | Lexapro, Prevacid, Vitamin cocktail (CO, Q10, E, C, B1, B2) | GI and behavioral issues | 20 | 7 |
| 32 | 81.2 | M | seizures, esophagitis, reflux, constipation, hypertyroidism, anxiety, bursitis, agitation, aggression, tiredness/low energy level | Depakote, propranolol, omeprazole, Singulair, Keppra, Risperdal, Synthroid | GI tract issues, reflux | 20 | 3 |
| 9 | 33 | M | stomach pains, GERD, increased acylcarnitine, auditory sensitivity, anxiety, recurrent mouth sores, allergic to eggs and soy | Vitamin B, C, omega fatty acids, Prevacid, Creon | GI concerns, anxiety, impulsivity | 15 | 1 |
| 6 | 25 | M | Landau-Kleffner Syndrome, grade 2 esophagitis, abdominal pain, confirmed | Periactin, Depakote, Prevacid, Singulair, Bentyl, | Significant abdominal pain, crying | 10 | 3 |

TABLE 1-continued

Baclofen Treatment in Autism Spectrum Disorder Patients

| | | | | | | | |
|---|---|---|---|---|---|---|---|
| 15 | 45.5 | M | metabolic diagnosis, possible migraines, crying episodes, regressions in HX anxiety | Donnatal, Vitamin cocktail, carafate, Milk of Magnesia Kondremal, Pentasa, Thazadose, Tenex | severe abdominal distress, constipation | 20 | 1 |
| 21 | 65 | F | Weekly seizures, severe abdominal distention/constipation, hypothyroid, respiratory distress | Depakote, Lamictal, levothyroxine, Prevacid | severe GI issue | 10 | <1 |
| 9 | 25 | M | Seizures, GERD, abdominal pain, constipation, esophagitis, rectum stromal fibrosis/reactive hyperplasia suggestive of mucosal prolapse, mitochondrial dysfunction, eczema | Singulair, Miralax, Prevacid, Lamictal, Tegretol, Diastat accudial, Vitamin cocktail, Pentasa | GI disorders | 10 | 8.5 |
| 14 | 33.2 | M | Seizures, ulcers, gastritis, esophagitis, diarrhea, constipation, GERD, GI nodular lymphoid hyperplasia, presumed mitochondrial disorder | Vitamin cocktail, Carafate, Lamictal, Tegretol, Prevacid, Singulair, Carnitine | GI tract issues, lethargy | 10 | 8.5 |
| 19 | 93 | M | increased CPK, anxiety, +PPD, −CXR | Carnitine, Celexa, Zyrtec, Nicomide, Risperdal, Adderall | behavioral symptoms, constipation, GERD | 10 | 7 |
| 8 | 26.4 | F | Daily seizures, reflux, abdominal pain, orthopedic disabilities (wheel chair confined) | Prevacid, Pepcid, Carafate, Depakote, Lamictal, Miralax, Carnitor, Keppra | GI tract issues, irritability | 20 | <1 |
| 11 | 35.2 | F | non-specific colitis, irritable bowel, reflux, overgrowth syndrome, GI motility issues, metabolic/mitochondrial disorder, potential pernicious puberty, irritable bladder, minimal bilateral pelviectasis, sleep disturbance, oromotor apraxia, small pituitary | Dipentum, Ultrase MT 12, Pepto Bismol, Carb-Digest, Sporanox, Vitamin C, Magnesium, Ditropan, Miralax, Flagyl, Cardex | GI disorder/GU disorder, behavior | 10 | 5.5 |

| Age (Yrs) | Weight (kg) | Sex | Ongoing | Overall Improvement[1] | Areas of Improvement | Adverse Events/ Discontinuation |
|---|---|---|---|---|---|---|
| 14 | — | F | Y | Not Improved | calmer after first few weeks | None |
| 29 | — | M | Y | Not Improved | repetitive/self-stimulatory behaviors | None |

TABLE 1-continued

Baclofen Treatment in Autism Spectrum Disorder Patients

| | | | | | | |
|---|---|---|---|---|---|---|
| 37 | — | F | N | Not Improved | slightly calmer | hospitalized with sepsis from a UTI related to poor communication and side effects of risperidone (which pre-existed baclofen)/ baclofen discontinued |
| 15 | 59.1 | F | Y | Improved | calmer, brighter, decreased aggression, more compliant, decreased screaming | None |
| 14 | 50 | F | Y | Improved | calmer, happier appearance, decreased irritability, dramatic decrease in aggression (10 BID) | None |
| 4 | 22 | M | N | Not Improved | calm at first; zone out week 2-3, D/C by week 5 (questionable dosing during vacation) | increased loose stools/ not improved |
| 13 | 65.2 | M | N | Improved | easygoing, able to tolerate stress/transitions, behavior, more signing, able to sleep more/consistently, GI function more comfortable | None/ Discontinued baclofen to see if changes were directly related to baclofen (may re-start) |
| 12 | 50.1 | F | N | Not Improved | None | None/ No change |
| 9 | 50.7 | M | Y | Improved | Happier, improved articulation, initiates interactions, stomach better, increase in sounds (language) | "went back to old self on higher dose (10 BID) |
| 7 | 29.1 | M | Y | Not Improved | Improved mood, tolerates crowds, calmer, more social and interactive, sleeping through night, no sour stomach, decreased anxiety | None |
| 32 | 81.2 | M | Y | Not Improved | pleasant, increase in obsessions, especially music making, better transition, increase in | None |

TABLE 1-continued

Baclofen Treatment in Autism Spectrum Disorder Patients

| | | | | | | |
|---|---|---|---|---|---|---|
| 9 | 33 | M | Y | Not Improved | hand tremors, wants to be social, requires naps/sleeping better, increase in brief seizures (has history), ability to retrieve language/use more words improved mood, less aggressive, language improvement, improved BMs, more focused on environment, calmer | takes longer to fall asleep, slight increase in finger stims |
| 6 | 25 | M | N | Not Improved | elated/no pain, calmer, more interactive (all during first week); all symptoms returned despite dosage adjustments | otitis (a week after starting baclofen)/ major management issues with other medication |
| 15 | 45.5 | M | N | Worsened | More engaged, positive sleep change, BMs; all during 1st week only, then returned to baseline | increased hyperactivity; increased GI discomfort and crying after 1st week |
| 21 | 65 | F | N | Not Improved | None | more drowsy (discontinued) |
| 9 | 25 | M | Y | Improved | happier/more comfortable, behavior better, more alert, more social/interactive improved sleep, decreased seizures, decreased constipation, better able to stay on task | None |
| 14 | 33.2 | M | Y | Improved | happier, calmer, more focused, better control over body, more aware of surroundings, decrease in self-injurious behaviors with GI flare-ups, decreased seizures, decreased frequency/ severity of GI issues, improved toileting | hyperactivity (but "happy"), sleeping at school |
| 19 | 93 | M | Y | Improved | more even, not aggressive, less rocking, more | None |

TABLE 1-continued

Baclofen Treatment in Autism Spectrum Disorder Patients

| | | | | | | |
|---|---|---|---|---|---|---|
| 8 | 26.4 | F | N | Worsened | appropriate socially, constipation no longer an issue, more pleasant None | increased hyperactivity (discontinued) |
| 11 | 35.2 | F | Y | Not Improved | mood/affect, behavior, repetitive behaviors, social interaction, sleep, GI function (hard to rule out other variables), better bladder control | None |

[1]Clinician's overall impression of improvement with baclofen: Improved includes "much better" and "better"; Not Improved includes ""slightly better" and "no change"; Worsened includes "worse" and "much worse"

Example 5

Fragile X Syndrome

Racemic baclofen was administered to treat five (5) male subjects with fragile X syndrome (Table 2). These subjects had serious behavioral problems that were incompletely controlled with typical psychoactive medications. Baclofen was added to concomitant antipsychotic treatment in four (4) of the five (5) subjects. Doses were titrated from about 2.5 mg BID to a maximum of about 20 mg TID, with a maximum duration of about 4 months. Clinicians rated their overall impression of improvement with baclofen treatment on a seven category scale ranging from "much worse," "worse," "slightly worse," "no change," "slightly better," "better" or "much better". Subjects were considered "Improved" if the clinician rating was either "much better" or "better"; considered "Not Improved" if the rating was "slightly worse", "no change" or "slightly better"; and considered "Worsened" if rated "worse" or "much worse". Two of the 5 patients demonstrated an improvement in behavior, including less irritability, aggression and agitation. Other areas of improvement included increased class participation and decreased hyperactivity. Two subjects did not demonstrate obvious improvement and the dosing regimen is still being adjusted. One subject worsened as evidenced by excessive sleepiness, increased irritability, screaming and swearing and baclofen was discontinued.

TABLE 2

Baclofen Treatment in Fragile X Patients

| Age (Yrs) | Weight (kg) | Concomitant Medications | Reason for Baclofen Treatment | Maximum Total Daily Dose (mg) | Treatment Duration (months) | Ongoing | Overall Improvement[1] | Areas of Improvement |
|---|---|---|---|---|---|---|---|---|
| 6 | 27 | Abilify, Risperdal | Agitation, head-banging, fecal smearing | 10 | 4 | Y | Improved | Decreases in all aberrant behaviors; increased class participation |
| 17 | 68 | Zoloft | Severe aggression, self-abusive behavior, biting | 20 | 3.5 | Y | Improved | Decreased irritability and hyperactivity; fewer outbursts |
| 20 | 96 | Abilify, Celexa, Xanax, lithium | Aggression, yelling, cursing | 20 | 1 | N | Worsened | None |
| 21 | 76 | Abilify, Cogentin | Agitation, anxiety, vomiting | 60 | 3 | Y | Not Improved | Decreases in behaviors for 1$^{st}$ week of treatment |
| 26 | 61 | Abilify, Trileptal | Aggression, agitation | 30 | 2 | Y | Not Improved | Decreased outbursts for 3-4 weeks |

[1]Clinician's overall impression of improvement with baclofen: Improved includes "much better" and "better"; Not Improved includes ""slightly better" and "no change"; Worsened includes "worse" and "much worse"

Example 6

Treatment of Fragile X Knockout Mice with a GABA(B) Agonist

Racemic Baclofen

Commercially marketed baclofen (Sigma Chemical Co., St. Louis, Mo.) is a 50:50 racemic mixture of the R- and S-isomers. In order to better understand the binding affinity of racemic baclofen the Side Effect Database (SED) was licensed from Novascreen Biosciences Corporation (Hanover, Md.). The Side Effect Database includes 76 molecular targets screened against 10 μM racemic baclofen in duplicate. These targets may be key mediators of side effects of baclofen, off-target effects and therapeutic targets. According to the Side Effect Database, baclofen was found to be selective for GABA-B and to less than about 50% binding at 10 μM to the other 75 molecular targets.

The experiments described herein in these preclinical studies demonstrate efficacy for racemic baclofen on a wide range of pharmacologic, physiologic and behavioral assays. Racemic baclofen reduces marble burying behavior in Fmr1 knockout mice (FIG. 1). Marble burying behavior is believed to reflect anxiety related, obsessive/compulsive and perseverative responding and, thus, mimics symptoms commonly observed in subjects with fragile X syndrome and other disorders of brain development.

R-Baclofen

The R-isomer of baclofen (R-baclofen) is a more potent GABA-B agonist than the S-isomer. The binding affinity for the R-(about 99% R-baclofen) and S-(about 99% S-baclofen) isomers of baclofen (purchased from Sigma Chemical Co., St. Louis, Mo.) was assessed. Both R- and S-baclofen were assayed at 10 μM in duplicate against 74 molecular targets (29 neurotransmitter related targets, 1 steroid, 3 ion channels, 1 second messenger, 4 growth factors/hormones, 13 brain/gut peptides, 12 general enzymes, 9 kinases, and 2 cell based and functional targets). Testing confirmed that R- and S-baclofen are selective agonists of GABA-B and also that the R-isomer is a more potent GABA-B agonist than the S-isomer (Table 3). As shown in Table 3 GABA(B) binding assay was performed using rat cortical membranes. IC50 and Ki values indicate that R-baclofen is about 10 to about 15 times more potent than S-baclofen and R-/S-baclofen is intermediate in potency.

TABLE 3

| Isomer(s) | IC50 | Ki |
| --- | --- | --- |
| R-baclofen | $1.23 \times 10^{-6}$ | $6.24 \times 10^{-7}$ |
| S-baclofen | $1.66 \times 10^{-5}$ | $8.59 \times 10^{-6}$ |
| R-/S-baclofen | $2.96 \times 10^{-6}$ | $1.51 \times 10^{-6}$ |

Figure 2:
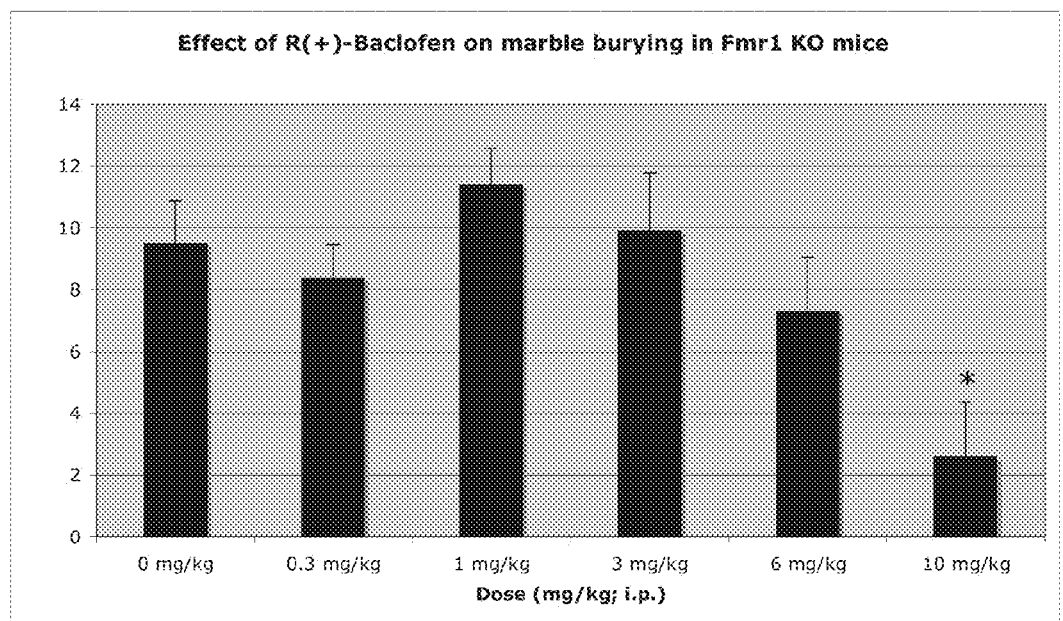
FIG. 2 depicts the effects of R(+)-baclofen on marble-burying behavior in Fmr1 KO mice (n=10-16 mice/group). Data are expressed as the mean marbles buried±SEM. An asterik (*) indicates data for the 10 mg/kg dose was significantly less (p<0.05) than all other groups.
Figure 3:
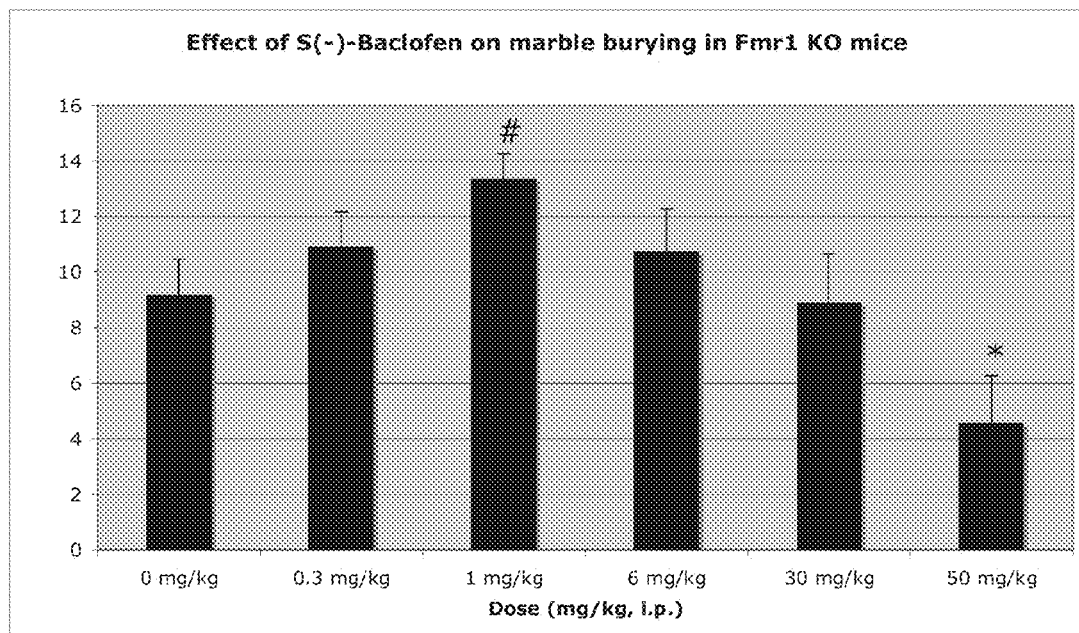
FIG. 3 depicts the effects S(−)-baclofen on marble-burying behavior of Fmr1 KO mice (n=11-15 mice/group). Data are expressed as the mean number of marbles buried±SEM. The # symbol indicates that the data for the 1 mg/kg dose was significantly greater than the 0 mg/kg dose. The asterik (*) indicates that the 50 mg/kg dose was significantly different (p<0.05) than all other groups.

Dose-response relationships for racemic (R-/S-) baclofen and each of the single isomers (R- or S-baclofen) on marble burying behavior was assessed. R-baclofen was more potent than S-baclofen as an inhibitor of marble-burying behavior (FIGS. 2 and 3). Marble burying behavior is believed to reflect anxiety related, obsessive/compulsive and perseverative behavior and thus mimic symptoms commonly observed in subjects with fragile X syndrome (FXS) and other disorders of brain development.

Figure 4:
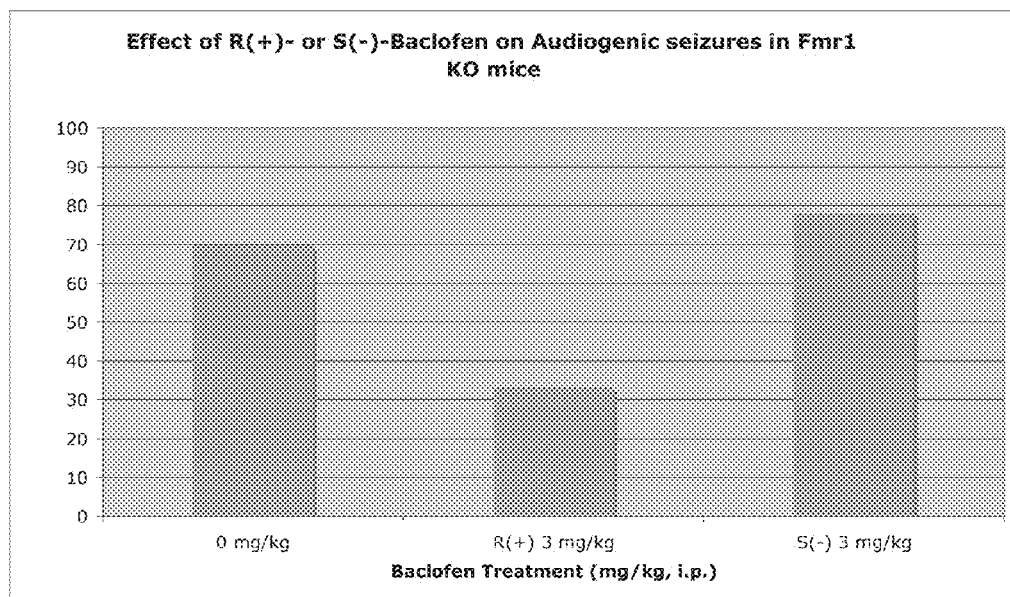
FIG. 4 depicts the effect of R(+)-baclofen and S(−)-baclofen on audiogenic seizures in Fmr1 KO mice (n=9-10 mice/group). Data are expressed as a percentage of mice treated with vehicle (0 mg/kg), R(+)- or S(−)-baclofen, that exhibited audiogenic seizures.

R-baclofen is more potent for inhibition of audiogenic seizures than S-baclofen (FIG. 4). Increased susceptibility to audiogenic seizures in Fmr1 knockout (KO) mice is believed to model the increased prevalence of seizure disorders in subjects with fragile X syndrome.

Marble Burying Assay
Experimental Aim

The goal of the experiment was to determine if marble-burying behavior is reduced following administration of the GABA-B receptor agonist R-baclofen and/or S-baclofen. In these experiments, Fmr1 KO mice received an i.p. injection of either R-baclofen or S-baclofen and were tested for marble-burying behavior.

Results

The results of the experiment demonstrate that R-baclofen and S-baclofen alter marble-burying behavior in Fmr1 KO mice. There was a significant dose-related alteration in marble burying behavior in Fmr1 KO mice that received an i.p. injection of R-baclofen 1 hr. before testing. Specifically, Fmr1 KO mice that received a dose of 10 mg/kg buried significantly less marbles than mice that received 0, 0.3, 1, 3, or 6 mg/kg. There was also a significant dose-related alteration in marble burying behavior in Fmr1 KO mice that received an i.p. injection of S-baclofen 1 hr. before testing. Specifically, mice that received 1.0 mg/kg buried significantly more marbles than 0.0 mg/kg treated mice. In addition, mice that received 50 mg/kg buried less marbles then mice receiving 0, 0.3, 1, 6 or 30 mg/kg S-baclofen.

Conclusions

The findings from this experiment indicate that there is a dose related reduction in marble burying behavior in Fmr1 KO mice treated with R-baclofen indicating that R-baclofen reduces the types of anxiety-like/obsessive/repetitive behaviors assessed in this assay. In addition, S-baclofen altered marble-burying behavior in a dose related manner, however, at the 1 mg/kg dose. Fmr1 KO mice actually buried more marbles, suggesting that this dose may have an effect opposite to the desired effect. Fmr1 KO mice that received about a 50 mg/kg dose, buried fewer marbles indicating that this high dose reduces this type anxiety-like/obsessive/repetitive behaviors assessed in this assay. These data indicate that R-baclofen may be more suitable than S-baclofen for reducing this type of anxiety-like/obsessive/repetitive behaviors simulated by the marble burying test.

Fragile X (Fmr1), Knock Out (KO) Mice

Fmr1 KO mice on a C57BL/6J (9 generations) genetic background were provided by The Jackson Laboratory (Bar Harbor, Me.). C57BL/6J was backcrossed to establish N11 generation Fmr1 mice. All mice for the current study were generated by mating Fmr1 heterozygous female mice with Fmr1 wild-type male mice. Only male Fmr1 KO (Fmr1$^{-/y}$) mice were tested in this study. Mice were housed 2-5 per cage in a room with a 12 hr light: dark cycle (lights on at 6 AM, off at 6 PM) with access to food and water ad libitum. Male mice that were 2-4 months of age (20-30 grams) were used for all experiments. In general, behavioral testing was performed between 9 AM and 3 PM. At the start of testing the mice were 3-4 months of age. An experimenter who was blind to the genotypes of the mice conducted the experiments.

Animals were genotyped by standard PCR techniques. For detection of the Fmr1 WT allele (527 bp product), PCR was performed on DNA from tails with primers Fmr1_S1 (5'GTGGTTAGCTAAAGTGAGGATGAT-3'; SEQ ID NO: 1) and Fmr1_S2 (5'CAGGTTTGTTGGGATTAACAGATC-3'; SEQ ID NO: 2). The Fmr1 KO allele (501 bp product) was detected by PCR with the Fmr1_S1 primer and primer Fmr1_N2 (5'TGGGCTCTATGGCTTCTGA-3'; SEQ ID NO: 3) which binds to a Neo cassette that replaced exon 5 of the Fmr1 gene. Cycle conditions were identical for both S1/S2 and S1/N2 combinations: 2 min at 94° C., 30 s at 55° C., 60 s at 72° C.), 10 min at 72° C. using standard PCR reagents.

Methods

A standard mouse cage was filled with 10 cm of corn-cob bedding. Twenty (20) small (1.5-2 cm) black marbles was placed equidistant (about 1-2 cm apart) on top of the bedding. A mouse was placed in the cage and allowed to explore and burry the marbles. After about 20 minutes the mouse was removed and the number of marbles buried (a marble is said to be "buried" if more than 50% of it is under the bedding) was recorded.

Baclofen and placebo were administered to the mice one hour prior to training, by intraperitoneal (i.p.) injections, in a volume of 0.1 ml/10 mg body weight.

Mice were injected (i.p.) with a dose of R(+)- or S(−)-baclofen one hour before testing. Each mouse was injected with a dose of R or S before testing. The order of treatment (e.g., R followed by S, or S followed by R) was balanced, and the dose was randomly assigned for each drug. There were at least 3 days between tests.

At the time of the test, a mouse was placed at an end of the cage containing marbles and allowed 20 minutes to bury marbles. After the 20-minute test, the mice were removed and the marbles buried were counted. A marble was identified as 'buried' if at least about 50% of it was covered with bedding. After testing mice were returned to their home cage. The following number (N) of mice were used for the various R(+)-baclofen doses: N=16, 0 mg/kg; N=15, 0.3 mg/kg; N=15, 1.0 mg/kg; N=10, 3.0 mg/kg; N=13, 6.0 mg/kg; N=10, 10 mg/kg. The following number (N) of mice were used for the various S(−)-baclofen doses: N=15, 0 mg/kg; N=13, 0.3 mg/kg; N=14, 1.0 mg/kg; N=12, 6.0 mg/kg; N=11, 30.0 mg/kg; N=14, 50 mg/kg.

Marbles buried were manually scored on a data sheet by an experimenter that was blind to the genotype and treatment. The data were then manually entered into a computer-spreadsheet.

The data were analyzed with a two-way (dose X treatment order) ANOVA. Significant main effects of dose were then analyzed using Least Square follow-up comparisons. Statistical analyses were analyzed using SPSS 11.0.

Results

Racemic Baclofen

Administration of racemic baclofen (6 mg/kg, 12 mg/kg) to fragile X knockout mice reduced marble burying behavior in a dose dependent manner (FIG. 1).

R(+)-Baclofen

FIG. 2 shows that there was a significant ($p<0.005$) dose-related alteration in marble burying behavior in Fmr1 KO mice that received an i.p. injection of R-baclofen one hour before testing. Specifically, Fmr1 KO mice that received a dose of 10 mg/kg buried significantly less ($p<0.05$) marbles then mice that received 0, 0.3, 1, 3, or 6 mg/kg. The effect of treatment order was not statistically significant ($p>0.05$).

S(−)-Baclofen

FIG. 3 shows that there was also a significant ($p<0.005$) dose-related alteration in marble burying behavior in Fmr1 KO mice that received an i.p. injection of S-baclofen one hour before testing. Specifically, mice that received 1.0 mg/kg buried significantly ($p<0.05$) more marbles than 0.0 mg/kg treated mice. In addition, mice that received 50 mg/kg buried significantly less ($p's<0.05$) marbles then mice receiving 0, 0.3, 1, 6, or 30 mg/kg S-baclofen. The effect of treatment order was not statistically significant ($p>0.05$).

Conclusion

The findings from this experiment indicate that there is a dose related reduction in marble burying behavior in Fmr1 KO mice treated with racemic baclofen. When administered separately, R-baclofen reduces the types of anxiety-like/obsessive/repetitive behaviors assessed in this assay. S-baclofen also altered marble-burying behavior in a dose related manner, however, at the 1 mg/kg dose, Fmr1 KO mice actually buried more marbles, suggesting that this dose may have an effect opposite to the desired effect. Fmr1 KO mice that received a 50 mg/kg dose, however, did bury fewer marbles indicating that this high dose reduces the types anxiety-like/obsessive/repetitive behaviors assessed in this assay. Together the findings suggest that R-baclofen may be more suitable than S-baclofen for reducing the type of anxiety-like/obsessive/repetitive behaviors simulated by the marble test.

Audiogenic Seizure Assay

Experimental Aim

The goal of the experiment was to determine if the sensitivity to audiogenic seizures in are reduced in Fmr1 KO mice following administration of the GABA-B receptor agonist R-baclofen and/or S-baclofen. In these experiments, Fmr1 KO mice received an i.p. injection of either R-baclofen or S-baclofen and tested for the audiogenic seizures.

Results

The results of the experiment demonstrate that R(+)-baclofen, but not S(−)-baclofen, reduces audiogenic seizures in Fmr1 KO mice. About 70-80% of vehicle-treated and S(−)-baclofen-treated (3 mg/kg) Fmr1 KO mice display an audiogenic seizure. In contract, only 33% of Fmr1 KO mice treated with 3 mg/kg R(+)baclofen display seizures.

Conclusions

The findings show that that R(+)-baclofen, but not S(−)-baclofen, reduced audiogenic seizures in Fmr1 KO mice and that R-baclofen is more effective than S-baclofen for reducing this type of environmentally-induced seizure in Fmr1 KO mice.

Methods

The methods employed in audiogenic seizure experiments as previously described (Yan, Q. J., et al., *Genes Brain Behav.* 3:337-359 (2004); Yan, Q. J., et al., *Neuropharm.* 49:1053-1066 (2005)). Briefly, Fmr1 knockout mice were treated i.p. with either vehicle, R-baclofen or S-baclofen about 60 minutes prior to the assay. Mice were exposed to a high intensity sound and then observed for occurrence of seizures. The primary endpoint was frequency of status epilepticus, a sustained tonic seizure most often resulting in respiratory arrest and death.

Test and control articles were administered to the mice one hour prior to training, via intraperitoneal (i.p.) injections, in a volume of 0.1 ml/10 g body weight.

Mice were injected (i.p.) with a dose of R(+)- or S(−)-baclofen 45-min before testing. Each mouse was injected with a dose of R or S before testing. Mice used for this study were experimentally naive.

Two-three mice were placed into a clean cage with bedding and transferred from their holding cage into a sound attenuated chamber. The cage was placed under a lid that contained two Radio Shack Personal Alarms. After 1 min the alarm sound was turned on for two minutes. After this two-minute exposure mice were given another minute of no sound followed by a second two-minute alarm. The presence of seizures as defined by 'non-startling' wild-running or tonic/clonic seizures were recorded. In our test protocol, mice do not display a seizure during the first alarm period.

The following number (N) of mice were used for the study: 0 mg/kg N=10; 3 mg/kg R(+)-baclofen N=9; and 3 mg/kg S(−)-baclofen N=9.

The presence of seizures as defined by 'non-startling' wild-running or tonic/clonic seizures were recorded. In addition, the latency to wild-running and/or tonic/clonic seizures was recorded. The percentage of mice displaying seizures was analyzed using SPSS 11.0.

Results

R-baclofen (3 mg/kg) significantly prevented induction of audiogenic seizures whereas S-baclofen at the same dose was no more effective than vehicle (FIG. 4).

FIG. 4 shows that about 70% of vehicle-treated Fmr1 KO mice displayed audiogenic seizures. Similarly, about 78% of Fmr1 KO mice treated with about 3 mg/kg S(−)-baclofen displayed seizures. In contract, only about 33% of Fmr1 KO mice treated with 3 mg/kg R(+)-baclofen displayed seizures.

Conclusion

These findings suggest that R-baclofen is likely to be more effective than S-baclofen for reducing this type of environmentally-induced seizure in Fmr1 KO mice.

Open Field Testing

Experimental Aim

The goal of the experiment was to determine if open-field activity in Fmr1 KO mice is altered following administration of the GABA-B receptor agonist R-baclofen and/or S-baclofen. In these experiments, Fmr1 KO mice received an i.p. injection of either R-baclofen or S-baclofen and tested for open-field activity.

Results

The results of the experiment demonstrate that R(+)-baclofen and S(−)-baclofen reduced open-field activity in Fmr1 KO mice. Relative to vehicle-treated wild type (WT) littermate controls, vehicle-treated Fmr1 KO mice were significantly more active in the open-field as measured by total activity. There was a significant dose-related reduction in exploratory activity as measured by total distance in Fmr1 KO mice that received an i.p. injection of R(+)- or S(−)-baclofen 1 hr before testing. Specifically, Fmr1 KO mice that received a dose of 6 mg/kg R(+)-baclofen were less active (reduced in total distance) compared to Fmr1 KO mice that received vehicle. Similarly, Fmr1 KO mice that received a dose of 50 mg/kg R(+)-baclofen were less active (reduced total distance) compared to Fmr1 KO mice that received vehicle.

Conclusions

These data show that there was a dose related reduction in exploratory activity in Fmr1 KO mice treated with R(+)- or S(−)-baclofen. Similar to individuals with fragile X syndrome, male Fmr1-deficient mice were more active, but this increased activity as measured by the total distance traveled in the open-field arena, can be normalized by baclofen. The data suggest that the dose required for S-baclofen that reduces exploratory activity in Fmr1 KO mice is greater than that required for R-baclofen-treated mice. Thus, R-baclofen may be more effective than S-baclofen for reducing the type of increased activity stimulated by the open-field test.

Methods

Test and control articles were administered to the mice one hour prior to training, via intraperitoneal (i.p.) injections, in a volume of 0.1 ml/10 g body weight.

Mice were injected (i.p.) with a dose of R(+)- or S(−)-baclofen one hour before testing. Each mouse was injected with a dose of R or S before testing. The order of treatment (e.g. R followed by S, or S followed by R) was balanced, and the dose was randomly assigned for each drug. There were at least 3 days between tests. Mice used for this experiment had been previously tested approximately one week earlier on the marble-burying test following treatment with R(+)- and S(−)-baclofen.

Mice were placed into the center of a clear Plexiglas (40 cm×40 cm×30 cm) open-field arena and allowed to explore for 30 minutes. Bright, overhead lighting provided approximately 800 lux of illumination inside the arenas. White noise was present at approximately 55 dB inside the arenas. Total distance traveled data during the 30 minute test were collected in two-min intervals by a computer-operated Digiscan optical animal activity system (Accuscan Electronics), but the data for the full 30-min test were analyzed.

The following number (N) of mice were used for the various R(+)-baclofen doses: N=12, 0 mg/kg; N=13, 1.0 mg/kg; N=13, 6.0 mg/kg. The following N were used for the various S(−)-baclofen doses: N=12, 0 mg/kg; N=14, 1.0 mg/kg; N=12, 50 mg/kg. The N for the WT littermate controls were: R(+)-baclofen vehicle-treatment N=14; S(−)-baclofen vehicle-treatment N=16.

Open-field activity data were analyzed using a two-step process. First, the data from vehicle-treated WT and Fmr1 KO littermates were analyzed using a one-way ANOVA. Next, the Fmr1 KO data for the three doses of each compound were analyzed to determine if the treatment significantly alter the behavior of the Fmr1 KO mice. Statistical analyses were analyzed using SPSS 11.0

Results

R(+)-Baclofen

Figure 5:
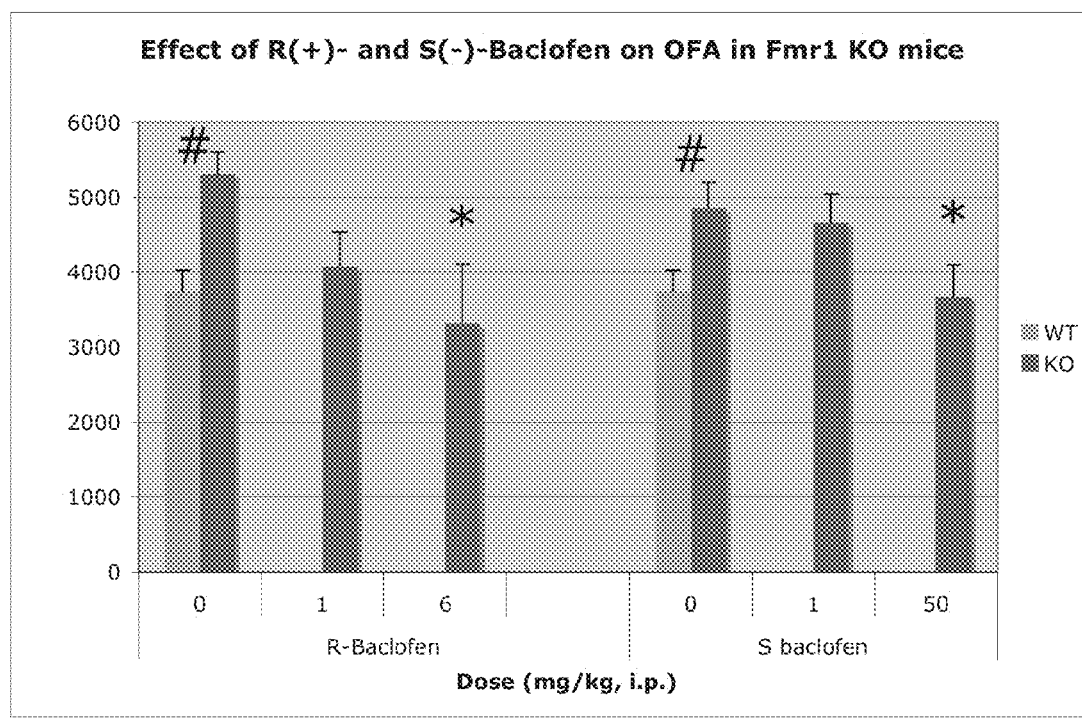
FIG. 5 depicts the effect of R(+)- and S(−)-baclofen on open-field activity of Fmr1 KO male mice. Data are expressed as the mean±SEM of the total distance traveled. The symbol # indicates that the data for the vehicle treated Fmr1 KO mice are significantly higher than wild type (WT) mice. An asterik (*) indicates that the vehicle-treated Fmr1 KO mice were significantly higher than the respective dose of R(+)- or (S−)-baclofen.

FIG. 5 shows that there was a significant ($p<0.001$) increase in locomotor activity in vehicle-treated Fmr1 KO mice compared to vehicle-treated WT controls. In addition, there was a dose-related alteration in total distance traveled in Fmr1 KO mice that received an i.p. injection of R-baclofen 1 hr before testing. Fmr1 KO mice that received a dose of 6 mg/kg were significantly less active ($p=0.018$) then mice than vehicle-treated Fmr1 KO mice.

S(−)-Baclofen

FIG. 5 shows that there was a significant ($p<0.05$) increase in locomotor activity in vehicle-treated Fmr1 KO mice compared to vehicle-treated wild type (WT) controls. In addition, there was a dose-related alteration in total distance traveled in Fmr1 KO mice that received an i.p. injection of S(−)-baclofen 1 hr before testing. Specifically, Fmr1 KO mice that received a dose of 50 mg/kg were significantly less active ($p=0.021$) then mice than vehicle-treated Fmr1 KO mice.

Conclusions

These data show there is a dose related reduction in locomotor activity in Fmr1 KO mice treated with R(+)-baclofen indicating that R(+)-baclofen reduces Fmr1 KO hyperactivity as assessed in this assay. In addition, S-baclofen reduced Fmr1 KO activity in a dose related manner. A lower dose of R(+)-baclofen was effective at reducing Fmr1 KO hyperactivity relative to S(−)-baclofen. R(+)-baclofen may be more suitable than S(−)-baclofen for reducing the type of hyperactivity in Fmr1 KO mice stimulated by the open-field test.

Pre-Clinical Summary

R-baclofen was more than 10-fold more potent than S-baclofen as a GABA-B agonist (Table 3) and also more potent for inhibition of marble-burying behavior (FIGS. 2 and 3). Similarly, R-baclofen is more potent for inhibition of audiogenic seizures than S-baclofen (FIG. 4) and open field testing (FIG. 5).

Example 7

Treatment of Fragile X Knock Out Mice with a M1 Muscarinic Receptor Antagonist

Figure 6:
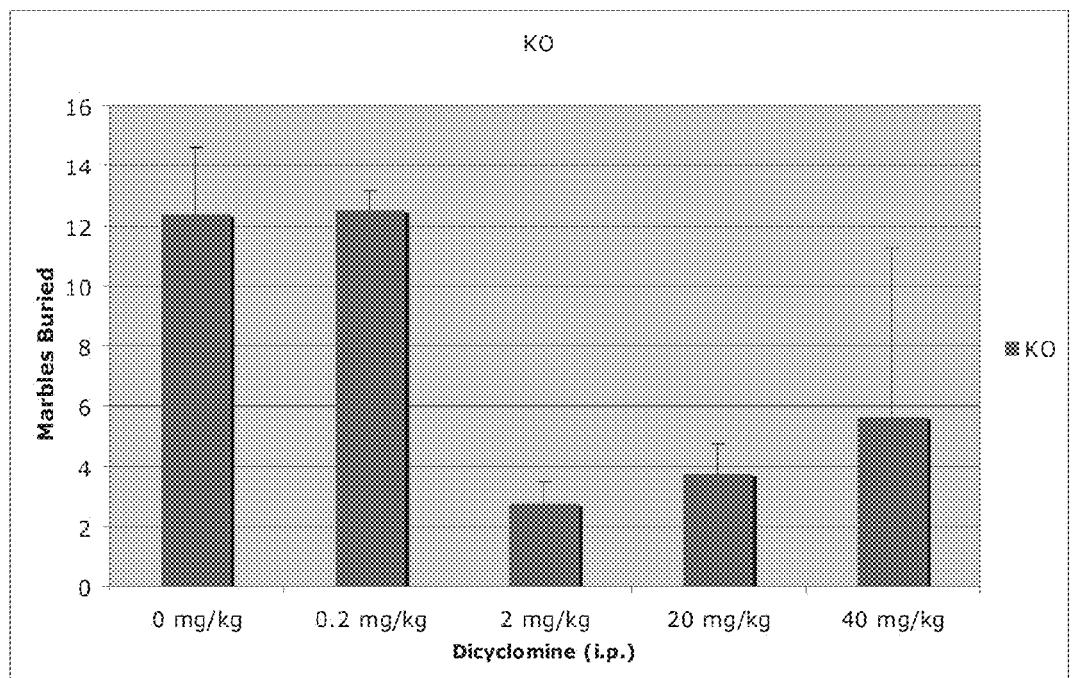
FIG. 6 depicts dicyclomine inhibition of marble-burying behavior in fragile X knockout (KO) mice (n=3-5 mice/group). Data are expressed as the mean number of marbles buried±SEM.
Figure 7:
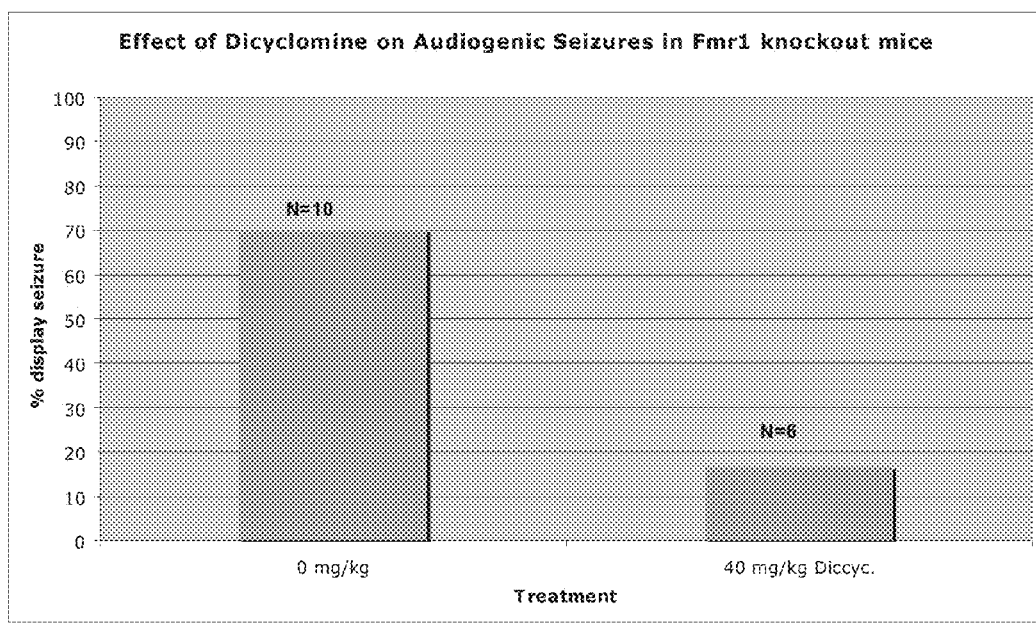
FIG. 7 depicts audiogenic seizures in young Fmr1 KO mice with or without dicyclomine (diccyc.) treatment. Data are the percentage of mice treated with vehicle (0 mg/kg) or dicyclomine (40 mg/kg) that displayed audiogenic seizures.

Dicyclomine reduces marble burying behavior in Fmr1 knockout mice (FIG. 6). Marble burying behavior is believed to reflect anxiety related, obsessive/compulsive and perseverative responding and thus mimic symptoms commonly observed in subjects with fragile X syndrome and other disorders of brain development. Similarly, dicyclomine inhibited audiogenic seizures in Fmr1 knockout mice (FIG. 7). Increased susceptibility to audiogenic seizures in Fmr1 knockout mice is believed to model the increased prevalence of seizure disorders in subjects with FXS.

Marble Burying Assay

Methods

Fmr1 KO mice were bred on a C57BL/6J genetic background. Only male Fmr1 KO (Fmr1−/y) mice were tested in this study. A standard mouse cage was filled with 10 cm of corn-cob bedding. Small (1.5-2 cm) black marbles were placed equidistant on top of the bedding. A mouse was placed in this cage and allowed to explore and bury the marbles. After about 20 minutes the mouse was removed and the number of marbles buried (a marble was considered 'buried' if more than about 50% of the marble under the bedding) was recorded. Mice were treated with dicyclomine about 60 minutes before the test.

Results

Fmr1 knockout mice in this background strain buried more marbles than wild type (wt) littermates. Administration of dicyclomine reduced marble burying behavior in a dose dependent manner (FIG. 6).

Conclusion

These data show that dicyclomine effectively rescues seizure in Fmr1 KO mice.

EQUIVALENTS

While this invention has been particularly shown and described with references to preferred embodiments thereof, it will be understood by those skilled in the art that various changes in form and details may be made therein without departing from the scope of the invention encompassed by the appended claims.

SEQUENCE LISTING

```
<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
gtggttagct aaagtgagga tgat                                      24

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
caggtttgtt gggattaaca gatc                                      24

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
tgggctctat ggcttctga                                            19
```

Conclusion

These data show there is a dose related reduction in marble burying behavior in Fmr1 KO mice treated with dicyclomine. Dicyclomine reduced the types of anxiety-like/obsessive/repetitive behaviors assessed in this assay.

Audiogenic Seizure Assay

Methods

The methods employed are described above. Briefly, Fmr1 knockout mice were treated i.p. with either vehicle or dicyclomine about 60 minutes prior to the assay. Mice were exposed to a high intensity sound and then observed for occurrence of seizures. The primary endpoint was frequency of status epilepticus, a sustained tonic seizure most often resulting in respiratory arrest and death.

Results

Dicyclomine significantly prevented induction of audiogenic seizures (FIG. 7).

What is claimed is:

1. A method of improving at least one of motivation, calmness, class participation, ability to tolerate stress and sleep patterns in a human having autism spectrum disorder, comprising the step of orally administering to the human a composition that includes a therapeutically effective amount of at least one GABA(B) agonist.

2. The method of claim 1, wherein the GABA(B) agonist is administered to the human in a dose of about 0.001 mg/kg/day to about 5 mg/kg/day.

3. The method of claim 1, wherein the GABA(B) agonist is administered to the human once a day.

4. The method of claim 1, wherein the GABA(B) agonist is administered to the human twice a day.

5. The method of claim 1, wherein the GABA(B) agonist is administered to the human in a dose of about 1 mg twice a day.

6. The method of claim 1, wherein the GABA(B) agonist is administered to the human in a dose of about 10 mg three times a day.

* * * * *

UNITED STATES PATENT AND TRADEMARK OFFICE
CERTIFICATE OF CORRECTION

| | |
|---|---|
| PATENT NO. | : 9,044,443 B2 |
| APPLICATION NO. | : 13/912874 |
| DATED | : June 2, 2015 |
| INVENTOR(S) | : Kathryn Roberts et al. |

It is certified that error appears in the above-identified patent and that said Letters Patent is hereby corrected as shown below:

On the Title Page, item (56):

In Other Publications:

At column 2, line number 23, delete "Neorologically" and insert --Neurologically--;

Page 2, at column 1, line number 13, delete "Refulx" and insert --Reflux--;

Page 2, at column 2, line number 33, delete "Comparision" and insert --Comparison--.

In the Specification:

At column 3, line number 24, delete "asterik" and insert --asterisk--;

At column 5, line number 33, delete " trifluormethoxybenzothiazole" and insert --trifluoromethoxybenzothiazole--;

At column 5, line number 49, delete "oxaylate," and insert --oxalate--;

At column 8, line number 40, delete "Adolsecent." and insert --Adolescent.--;

At column 8, line number 59, delete "dicylomine," and insert --dicyclomine,--;

At column 11, line number 2, delete "premutation" and insert --permutation--;

At column 12, line number 39, delete "brain Inhibition" and insert --brain. Inhibition--;

At column 13, line number 26, delete "(phenylthynyl)" and insert --(phenylethynyl)--;

Signed and Sealed this
First Day of December, 2015

Michelle K. Lee
*Director of the United States Patent and Trademark Office*

In the Specification:

At column 14, line number 19, delete "[4-5]" and insert --[4.5]--;

At column 14, line number 59, delete "Palmnitate;" and insert --Palmitate;--;

At column 14, line number 62, delete "Risperadone" and insert --Risperidone--;

At column 15, line number 64, delete "Mucarinic" and insert --Muscarinic--;

At column 15, line number 65, delete "pertussins" and insert --pertussis--;

At column 16, line number 25, delete "muscaranic" and insert --muscarinic--;

At column 17, line number 14, delete "anticholinergenic" and insert --anticholinergic--;

At column 17, line number 49, delete "ipratroprium" and insert --ipratropium--;

At column 18, line number 17, delete "Enantomerically" and insert --Enantiomerically--;

At column 18, line number 17, delete "S; d, 1)" and insert --S; d, I)--;

At column 21, line number 21, delete "enatomerically" and insert --enantiomerically--;

At column 21, line number 31, delete "enatomerically" and insert --enantiomerically--;

At column 21, line number 64, delete "auxillary" and insert --auxiliary--;

At column 24, line number 8, delete "gran mal" and insert --grand mal--;

At column 24, line number 18, delete "amitryptiline" and insert --amitriptyline--;

At column 24, line number 61, delete "Concommitant" and insert --Concomitant--;

At column 24, line number 63, delete "gran mal" and insert --grand mal--;

At column 25, line number 26, delete "(mean±SE)" and insert --(mean+SE)--;

At column 25, line number 31, delete "Concommitant" and insert --Concomitant--;

At columns 25-26, line number 7 (Table 1), delete "fluoxitine," and insert --fluoxetine,--;

At columns 27-28, line number 11 (Table 1-continued), delete "Trileptol," and insert --Trileptal,--;

At columns 27-28, line number 39 (Table 1-continued), delete "Donovex" and insert --Dovonex--;

CERTIFICATE OF CORRECTION (continued)
U.S. Pat. No. 9,044,443 B2

In the Specification:

At columns 27-28, line number 62 (Table 1-continued), delete "hypertyroidism," and insert --hyperthyroidism,--;

At columns 29-30, line number 8 (Table 1-continued), delete "Kondremal," and insert --Kondremul,--;

At column 40, line number 20, delete "that that" and insert --that--.